United States Patent
Higashi et al.

(10) Patent No.: US 7,045,950 B2
(45) Date of Patent: *May 16, 2006

(54) ORGANIC ELECTROLUMINESCENCE DEVICE WITH ORGANIC COMPOUND LAYER CONTAINING LOWER THAN 500 PPM OF A HALOGEN-CONTAINING COMPOUND

(75) Inventors: Hisahiro Higashi, Chiba (JP); Toshio Sakai, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/612,065

(22) Filed: Jul. 3, 2003

(65) Prior Publication Data

US 2004/0007971 A1    Jan. 15, 2004

Related U.S. Application Data

(62) Division of application No. 09/623,042, filed as application No. PCT/JP99/07201 on Dec. 22, 1999, now Pat. No. 6,617,051.

(30) Foreign Application Priority Data

Dec. 28, 1998 (JP) .................... 10-373029

(51) Int. Cl.
*H05B 33/14* (2006.01)

(52) U.S. Cl. ...................... 313/504; 428/690

(58) Field of Classification Search ............... 313/504, 313/506; 428/690, 917
See application file for complete search history.

(56) References Cited

U.S. PATENT DOCUMENTS

| | | | |
|---|---|---|---|
| 5,206,103 A | 4/1993 | Stolka et al. | |
| 5,466,392 A | 11/1995 | Hironaka et al. | |
| 5,558,904 A | 9/1996 | Hsieh et al. | |
| 5,886,209 A * | 3/1999 | Wettling et al. | 560/61 |
| 6,057,048 A | 5/2000 | Hu et al. | |
| 6,150,043 A * | 11/2000 | Thompson et al. | 428/690 |
| 6,169,163 B1 | 1/2001 | Woo et al. | |
| 2001/0019783 A1 | 9/2001 | Sakai et al. | |

FOREIGN PATENT DOCUMENTS

| | | |
|---|---|---|
| JP | 5-140145 | 6/1993 |
| JP | 7-150137 | 6/1995 |
| JP | 07-282977 | 10/1995 |
| JP | 9-232079 | 9/1997 |
| JP | 9-255774 | 9/1997 |
| JP | 10-25472 | 1/1998 |

OTHER PUBLICATIONS

PHalide, Grant and Hackh's Chemical Dictionary, 5th Edition, McGraw Hill, Inc. (1987), p. 273.

* cited by examiner

*Primary Examiner*—Karabi Guharay
(74) *Attorney, Agent, or Firm*—Oblon, Spivak, McClelland, Maier & Neustadt, P.C.

(57) ABSTRACT

The invention is an organic electroluminescent device that comprises organic compound layer(s) including at least one organic emitting layer sandwiched between a pair of electrodes, wherein at least one organic compound layer is formed from an organic compound material having an impurity concentration of lower than 1000 ppm. The device has the advantages of applicability to lightweight, thin and low-voltage driving displays, good luminescent capacity attenuating little even in long-term driving operation, and good durability.

5 Claims, No Drawings

ORGANIC ELECTROLUMINESCENCE DEVICE WITH ORGANIC COMPOUND LAYER CONTAINING LOWER THAN 500 PPM OF A HALOGEN-CONTAINING COMPOUND

TECHNICAL FIELD

The present invention relates to an organic electroluminescent device (hereinafter this will be referred to as an organic EL device). More precisely, the invention relates to an organic EL device having the advantages of applicability to lightweight, thin and low-voltage driving displays, good luminescent capacity attenuating little even in long-term driving operation, and good durability.

BACKGROUND ART

As being self-luminescent, organic electroluminescent, EL devices have high visibility. In addition, they have high impact resistance as being completely solid devices. Therefore, they are much used in various fields of thin-film display devices, back lights for liquid-crystal displays, flat light sources, etc.

Distributed electroluminescent devices are now in practical use. As they require alternating voltage of at least tens volts and 10 kHz or more, their driving circuits are complicated.

In the circumstances, organic EL devices capable of being driven at lowered voltage of 10 volts or so and capable of emitting high-luminance light are much studied these days. For example, thin-film organic EL devices having a multi-layered structure of transparent electrode/hole injection layer/emitting layer/back electrode are proposed in Appl. Phys. Lett., Vol. 51, pp. 913–915 (1987) by C. W. Tang and S. A. Van Slyke, and in Japanese Patent Laid-Open No. 264629/1988. These are so designed that the hole injection layer therein can efficiently inject holes into the emitting layer therein. The emitting layer in such organic EL devices may have a single-layered structure, which, however, could not enjoy well-balanced electron transportation and hole transportation. To solve the problem, the emitting layer is modified to have a multi-layered structure of improved performance.

However, the process of forming the multi-layered emitting layer is complicated and takes a lot of time. Another problem with it is that the multi-layered structure is against the recent tendency in the art which is toward reducing the thickness of layers constituting organic EL devices. On the other hand, down-sized, compact and portable information appliances are much desired these days, and they are required to be driven at low voltage. In the circumstances, various types of light-emitting materials and hole-transporting materials are tried for such lightweight, low-voltage driving appliances.

Further, the most important theme in practical studies of organic EL devices is to establish the technique of preventing the attenuation of the luminance of the devices in long-term driving and to provide practicable organic EL devices. In this respect, it is said that the purity of organic compounds to be used for producing constituent materials for organic EL devices has a great influence on the attenuation of the luminous efficiency and the luminance of the devices produced, for example, as in "Monthly Display, September, p. 15, 1995", and "Applied Physics, Vol. 66, No. 2, pp. 114–115, 1997". However, the influences of the structures and the properties of organic compounds to be used for producing organic EL devices on the properties of the devices produced are not as yet clarified, and no method has heretofore been established capable of quantitatively determining the influences in question.

In that situation, the object of the present invention is to provide an organic EL device having the advantages of applicability to lightweight, thin and low-voltage driving displays, good luminescent capacity attenuating little even in long-term driving operation, and good durability.

DISCLOSURE OF THE INVENTION

We, the present inventors have assiduously studied in order to attain the object as above, and, as a result, have found that the object can be attained by an organic EL device in which at least one organic compound layer comprises an organic compound material having an impurity concentration of smaller than 1000 ppm including 0 ppm. On the basis of this finding, we have completed the present invention.

Specifically, the invention is summarized as follows:

(1) An organic electroluminescent device that comprises organic compound layer(s) including at least one organic emitting layer sandwiched between a pair of electrodes, wherein at least one organic compound layer is formed from an organic compound material having an impurity concentration of lower than 1000 ppm.

(2) An organic electroluminescent device that comprises organic compound layer(s) including at least one organic emitting layer sandwiched between a pair of electrodes, wherein at least one organic compound layer is formed from an organic compound material having an impurity concentration of lower than 500 ppm and the impurity therein is a halogen-containing compound.

(3) The organic electroluminescent device of above (2), wherein the halogen-containing compound is a halogen compound.

(4) The organic electroluminescent device of any of above (1) to (3), wherein the organic compound layers are a hole injection layer, an organic emitting layer and an electron injection layer.

(5) The organic electroluminescent device of any of above (1) to (4), wherein at least one organic compound material to form the organic compound layer(s) is purified through sublimation.

(6) The organic electroluminescent device of any of above (1) to (4), wherein at least one organic compound material to form the organic compound layer(s) is purified through recrystallization or reprecipitation, or through recrystallization combined with reprecipitation.

(7) A method for selecting organic compound materials for organic electroluminescent devices, comprising determining, through high-performance liquid chromatography, the impurity content of each organic compound material to form organic compound layers for the devices, selecting those having an impurity content of smaller than 1000 ppm out of the materials analyzed, and using the thus-selected materials for forming the organic compound layers.

(8) A method for selecting organic compound materials for organic electroluminescent devices, comprising determining the impurity content of at least one organic compound material to form organic compound layers for the devices, selecting those having an impurity content of smaller than 1000 ppm out of the materials analyzed, and using the thus-selected materials for forming the organic compound layers.

(9) The method of above (7) or (8) for selecting organic compound materials for organic electroluminescent devices, wherein the impurity in the organic compound materials is a halogen-containing compound.

BEST MODES OF CARRYING OUT THE INVENTION

Modes of carrying out the invention are described hereinunder.

The invention is an organic EL device that comprises organic compound layer(s) including at least one organic emitting layer sandwiched between a pair of electrodes, wherein at least one organic compound layer is formed from an organic compound material having an impurity concentration of lower than 1000 ppm (by weight, but, as the case may be, by volume).

The organic EL device of the invention comprises organic compound layer(s) including at least one organic emitting layer sandwiched between a pair of electrodes. Its typical structures are mentioned below, but are not limitative.

<1> Anode/emitting layer/cathode

<2> Anode/hole injection layer/emitting layer/cathode

<3> Anode/emitting layer/electron injection layer/cathode

<4> Anode/hole injection layer/emitting layer/electron injection layer/cathode

<5> Anode/organic semiconductor layer/emitting layer/cathode

<6> Anode/organic semiconductor layer/electron barrier layer/emitting layer/cathode <7> Anode/organic semiconductor layer/emitting layer/adhesion improving layer/cathode <8> Anode/hole injection layer/hole transporting layer/emitting layer/electron injection layer/cathode The organic EL device of the invention may have any of these layer structures, but preferably has the layer structure <8>. The organic compound layers referred to herein include the emitting layers and others sandwiched between the anode and the cathode in the layer structures mentioned above. In the organic EL device of the invention, at least any one of these organic compound layers is formed from an organic compound material having an impurity concentration of lower than 1000 ppm.

The organic EL device is formed on a transparent substrate. The transparent substrate supports the organic EL device, and its transparency in a visible ray range of from 400 to 700 nm is preferably at least 50%. Also preferably, the substrate is flat and has a smooth surface.

Preferred examples of the transparent substrate of that type are glass plates, synthetic resin plates, etc. The glass plates may be made of, for example, soda-lime glass, barium-strontium glass, lead glass, aluminosilicate glass, borosilicate glass, barium borosilicate glass, quartz, etc. The synthetic resin plates may be made of, for example, polycarbonate resins, acrylic resins, polyethylene terephthalate resins, polyether sulfide resins, polysulfone resins, etc.

For the electrode material for the anode, preferred are metals, alloys, electroconductive materials and their mixtures having a large work function (at least 4 eV). Specific examples of the electrode material are metals such as Au, etc.; and electroconductive materials such as CuI, ITO, SnO$_2$, ZnO, etc. To form the anode, the electrode material is formed into a thin film through vapor deposition, sputtering or the like. For its properties, it is desirable that the anode through which the light from the emitting layer is taken out has a light transmittance of larger than 10%. Also preferably, the sheet resistance of the anode is at most hundreds Ω/square. Though depending on its material, the anode has a thickness generally falling between 10 nm and 1 μm, but preferably between 10 nm and 200 nm.

It is desirable that the emitting layer in the organic EL device of the invention has all the following functions.

<1> Hole and electron receiving function: This is to receive holes from anodes and hole injection layers and receive electrons from cathodes and electron injection layers while in an electric field.

<2> Hole and electron transporting function: This is to move the injected charges (electrons and holes) by the force of the electric field.

<3> Light emitting function: This is to provide a site for electron-hole recombination to emit light.

In the anode, the degree of hole injection may differ from that of electron injection, and the degree of hole transportation and that of electron transportation that are represented by hole and electron mobility may also differ from each other. Preferably, any one type of the charges is moved in the anode.

The light-emitting material in the organic EL device is principally an organic compound. Concretely, it includes the following compounds, any of which are used in the device depending on the desired color tone.

For example, for UV to violet emission, compounds of the following general formula [1] are preferred.

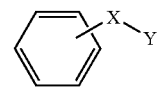

[1]

wherein X represents a group of the following general formula [2]:

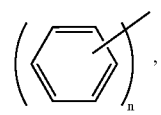

[2]

and Y represents a group of the following general formula [3]:

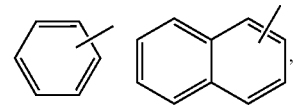

[3].

For the phenyl, phenylene and naphthyl groups in the compounds of formula [1], usable are compounds having one or more substituents such as an alkyl group having from 1 to 4 carbon atoms, an alkoxy group having from 1 to 4 carbon atoms, a hydroxyl group, a sulfonyl group, a carbonyl group, an amino group, a dimethylamino group, a diphenylamino group, etc. A plurality of these substituents, if any, may be bonded to each other to form a saturated 5-membered or 6-membered ring. Regarding their configuration, the phenyl, phenylene and naphthylene groups in the compounds are preferably para-positioned, since the bonding stability is good and since the compounds can be easily formed into flat and smooth films through vapor deposition. Specific examples of the compounds of formula [1] are mentioned below.

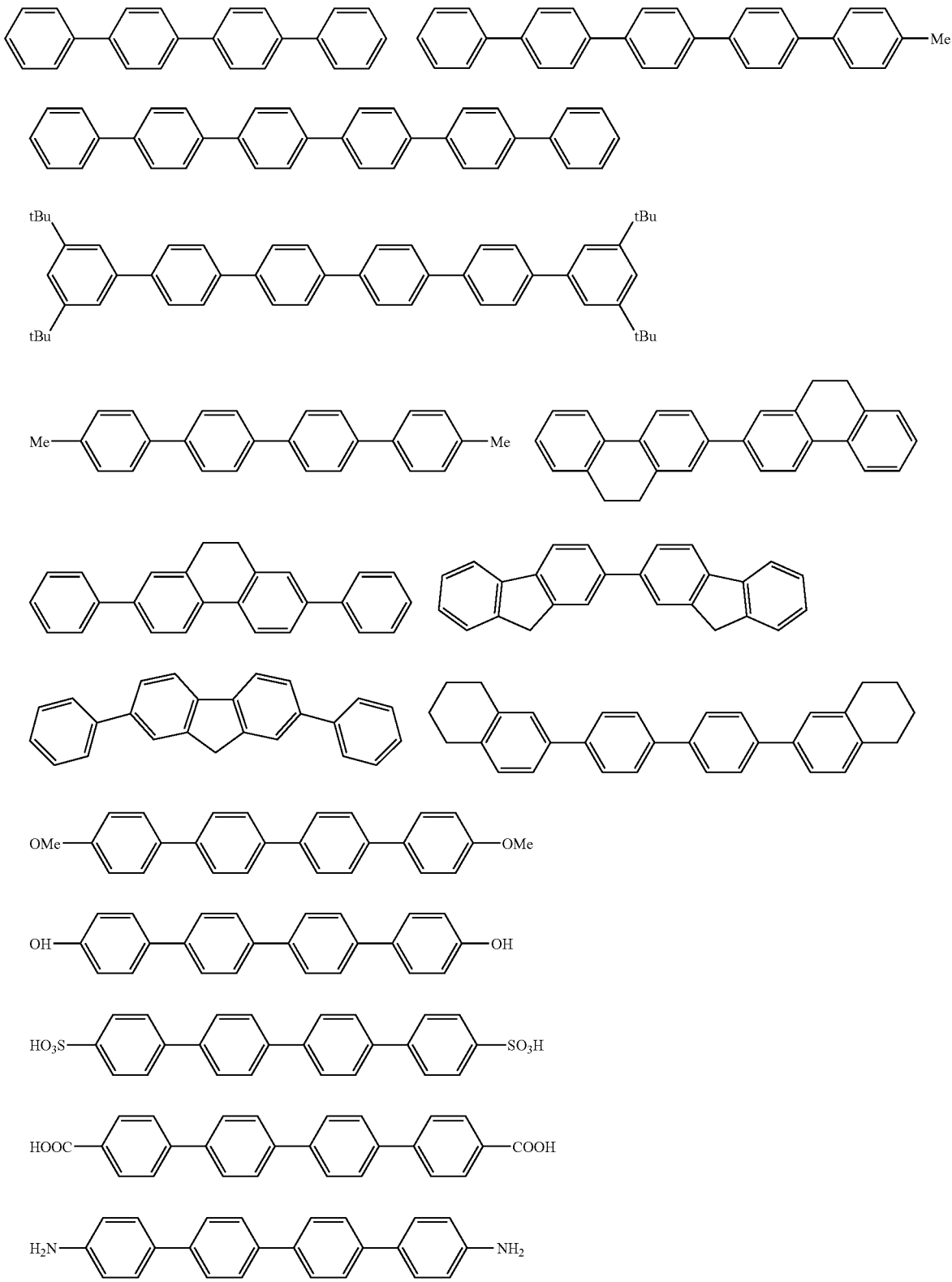

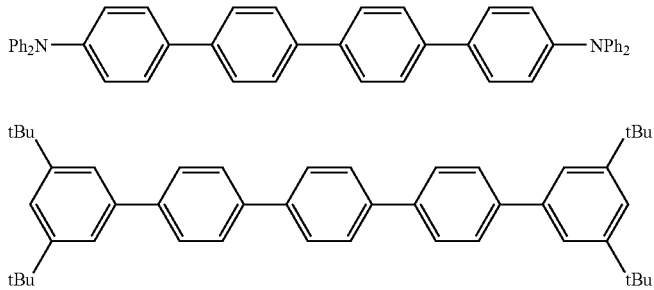

Of these compounds, especially preferred are p-quaterphenyl derivatives and p-quinquephenyl derivatives.

For blue to green emission, for example, employable are benzothiazole-type, benzimidazole-type, benzoxazole-type and other fluorescent brightening compounds, metal-chelated oxinoide compounds and styrylbenzene compounds. For these, for example, referred to are the compounds described Japanese Patent Laid-Open No. 194393/1984. Still other compounds usable herein are listed in Chemistry of Synthetic Dyes, 1971, pp. 628–637, and 640.

For the chelated oxinoide compounds, for example, usable are the compounds described in Japanese Patent Laid-Open No. 295695/1988. Typically, preferred are 8-hydroxyquinoline metal complexes such as tris(8-quinolinol) aluminium, etc., and also dilithiumepinetridione, etc.

For the styrylbenzene compounds, for example, usable are the compounds described in European Patents 0319881 and 0373582. Also usable for the material for the emitting layer are distyrylpyrazine derivatives such as those described in Japanese Patent Laid-Open No. 252793/1990. Apart from these, still usable for the material for the emitting layer are polyphenyl compounds such as those described in European Patent 0387715.

for the emitting layer are, for example, 12-phthaloperinone (in J. Appl. Phys., Vol. 27, L 713, 1988), 1,4-diphenyl-1,3-butadiene, 1,1,4,4-tetraphenyl-1,3-butadiene (both in Appl. Phys. Lett., Vol. 56, L 799, 1990), naphthalimide derivatives (in Japanese Patent Laid-Open No. 305886/1990), perylene derivatives (in Japanese Patent Laid-Open No. 189890/1990), oxadiazole derivatives (in Japanese Patent Laid-Open No. 216791/1990, or the oxadiazole derivatives disclosed by Hamada et al. in the 38th Applied Physics-related Joint Lecture Meeting), aldazine derivatives (in Japanese Patent Laid-Open No. 220393/1990), pyrazoline derivatives (in Japanese Patent Laid-Open No. 220394/1990), cyclopentadiene derivatives (in Japanese Patent Laid-Open No. 289675/1990), pyrrolopyrole derivatives (in Japanese Patent Laid-Open No. 296891/1990), styrylamine derivatives (Appl. Phys. Lett., Vol. 56, L 799, 1990), coumarin compounds (in Japanese Patent Laid-Open No. 191694/1990), polymer compounds such as those described in International Patent Publication WO90/13148 and Appl. Phys. Lett., Vol. 58, 18, P 1982, 1991, as well as 9,9',10,10'-tetraphenyl-2,2'-bianthracenes, PPV (polyparaphenylenevinylene) derivatives, polyfluorene derivatives and their polymers and others, for example, those having the following structures:

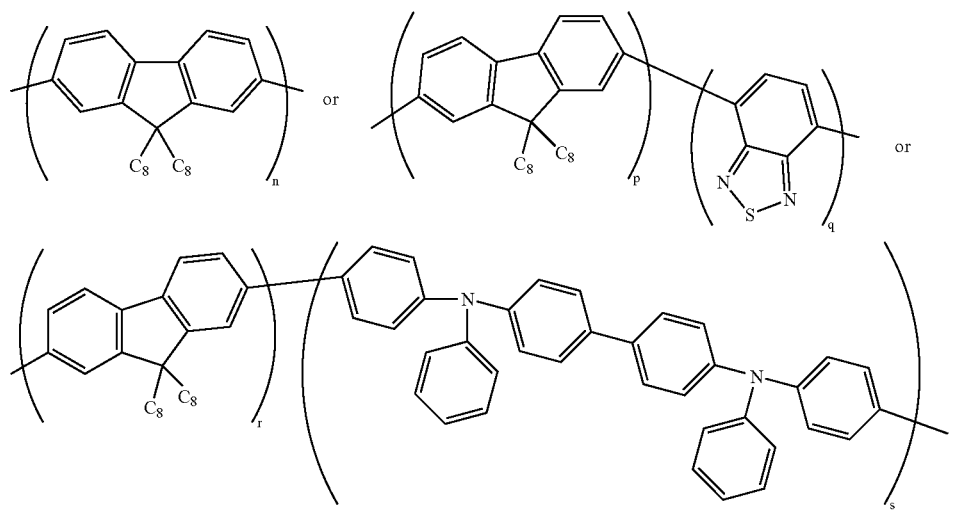

In addition to the fluorescent brightening agents, metal-chelated oxinoide compounds, styrylbenzene compounds and others mentioned above, further usable for the material and also 9,10-bis (N-(4-(2-phenylvinyl-1-yl)phenyl-N-phenylamino)anthracene, etc. Moreover, phenylanthracene derivatives of the following formula, such as those described in Japanese Patent Laid-Open No. 12600/1996 are also usable for light-emitting materials.

A1-L-A2 wherein A1 and A2 each represent a monophenylanthryl or diphenylanthryl group, and these may be the same or different; and L represents a single bond or a divalent linking group.

Especially preferred are phenylanthracene derivatives of the following general formulae:

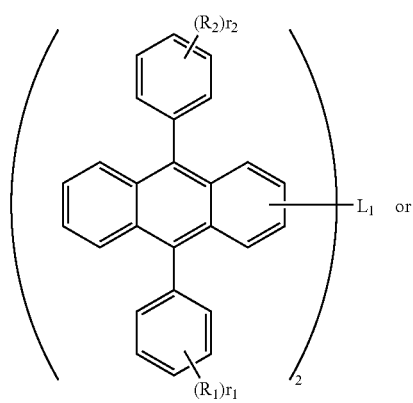

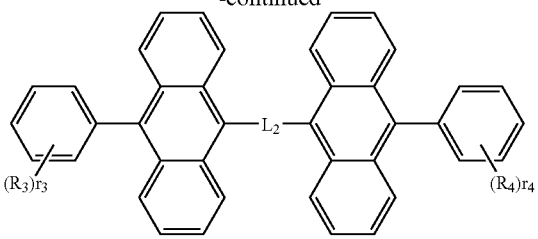

wherein $R_1$ and $R_2$ each represent an alkyl group, a cycloalkyl group, an aryl group, an alkenyl group, an alkoxy group, an aryloxy group, an amino group, or a heterocyclic group, and they may be the same or different; $r_1$ and $r_2$ each indicate 0 or an integer of from 1 to 5; when $r_1$ and $r_2$ each are an integer of 2 or more, the groups of $R_1$'s and $R_2$'s each may be the same or different, and $R_1$'s and $R_2$'s may be bonded to each other to form a ring; $L_1$ represents a single bond or an arylene group, and the arylene group may be interrupted by an alkylene group, —O—, —S— or —NR— (where R indicates an alkyl or aryl group) existing therein; $R_3$ and $R_4$ each represent an alkyl group, a cycloalkyl group, an aryl group, an alkenyl group, an alkoxy group, an aryloxy group, an amino group, or a heterocyclic group, and they may be the same or different; $r_3$ and $r_4$ each indicate 0 or an integer of from 1 to 5; when $r_3$ and $r_4$ each are an integer of 2 or more, the groups of $R_3$'s and $R_4$'s each may be the same or different, and $R_3$'s and $R_4$'s may be bonded to each other to form a ring; $L_2$ represents a single bond or an arylene group, and the arylene group may be interrupted by an alkylene group, —O—, —S— or —NR— (where R indicates an alkyl or aryl group) existing therein.

Specific examples of such anthracenes or phenylanthracenes are described below.

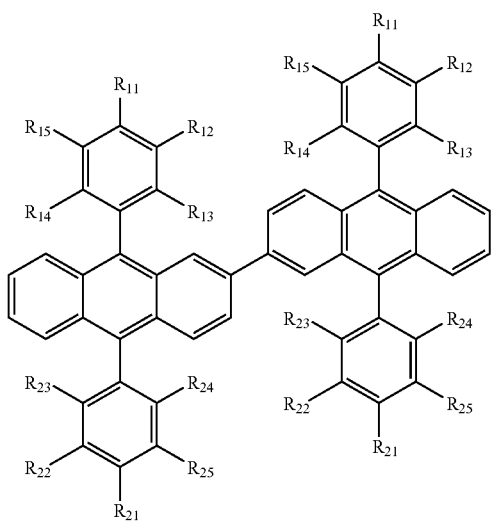

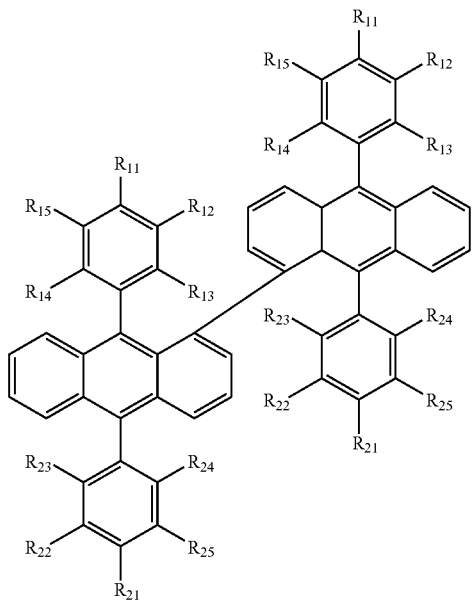

-continued
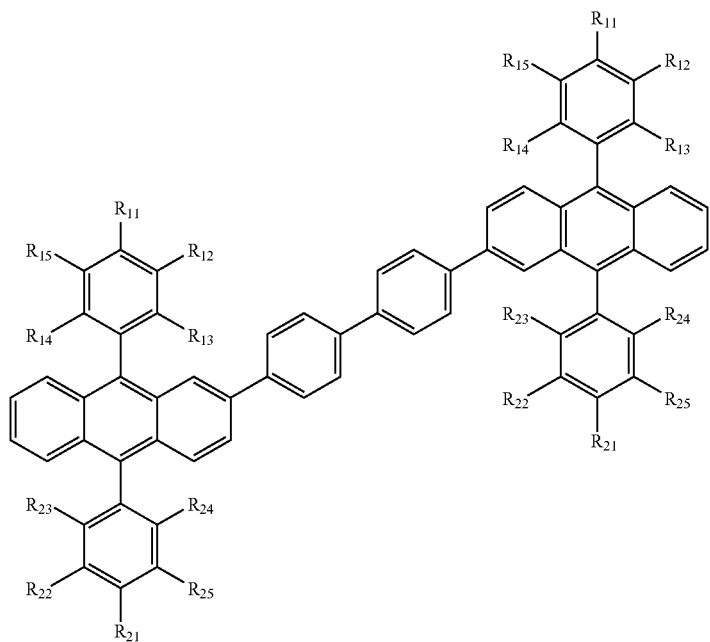
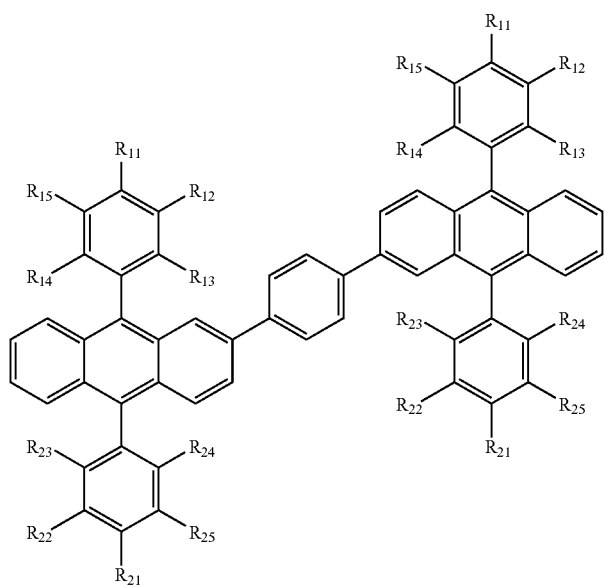
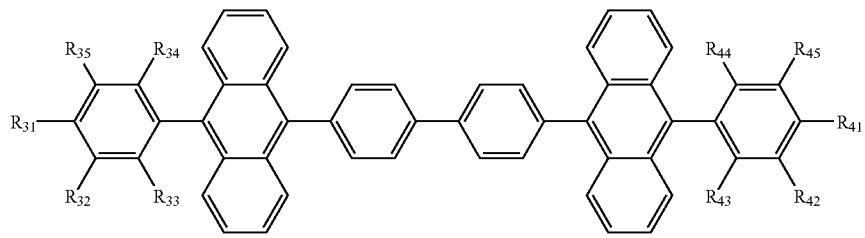
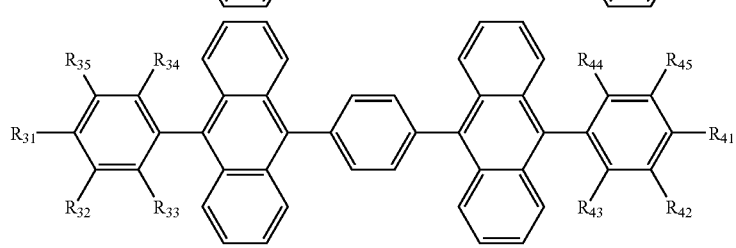

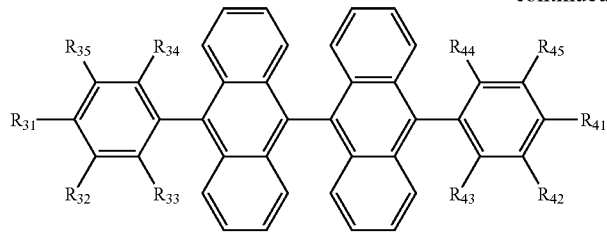
In these formulae, $R_{11}$ to $R_{45}$ each represent an alkyl group, a cycloalkyl group, an aryl group, an alkenyl group, an alkoxy group, an aryloxy group, an amino group, or a heterocyclic group; and they may be the same or different.
Further mentioned are the following compounds:
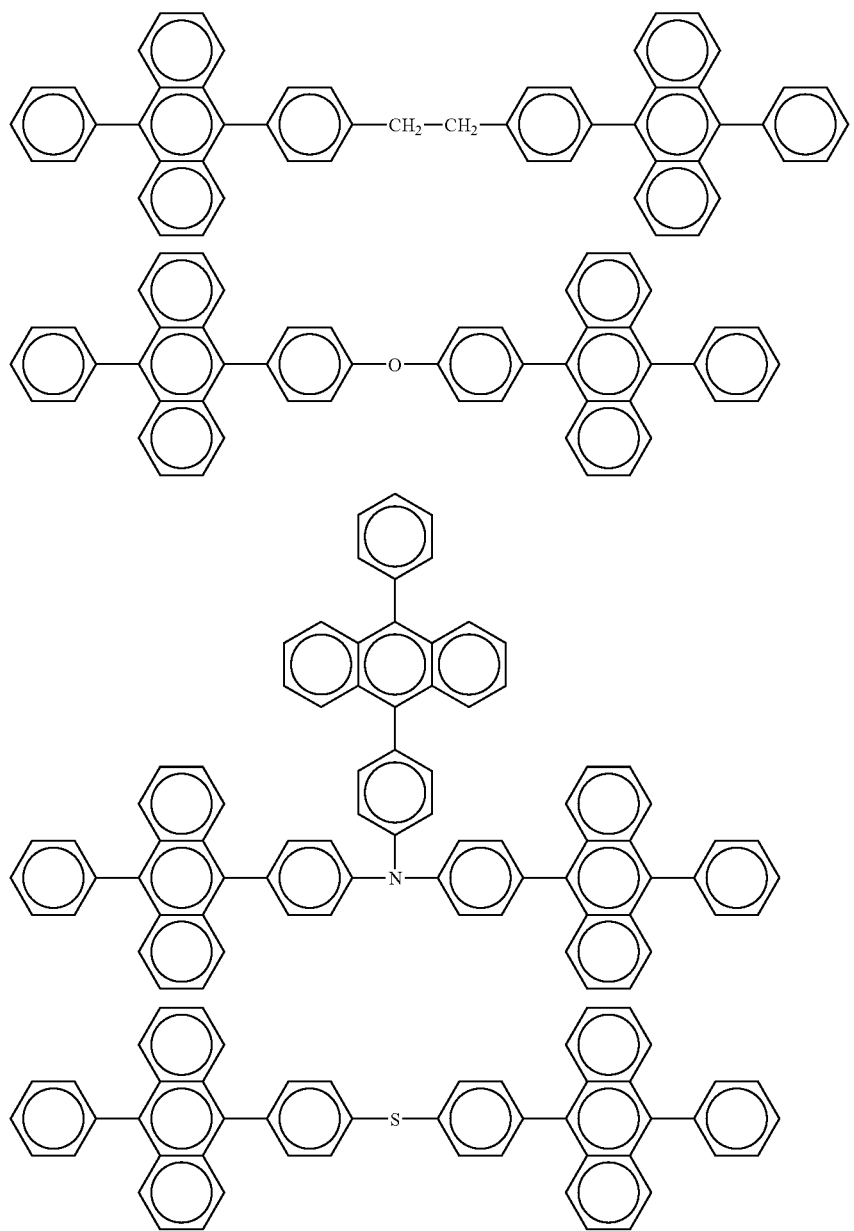

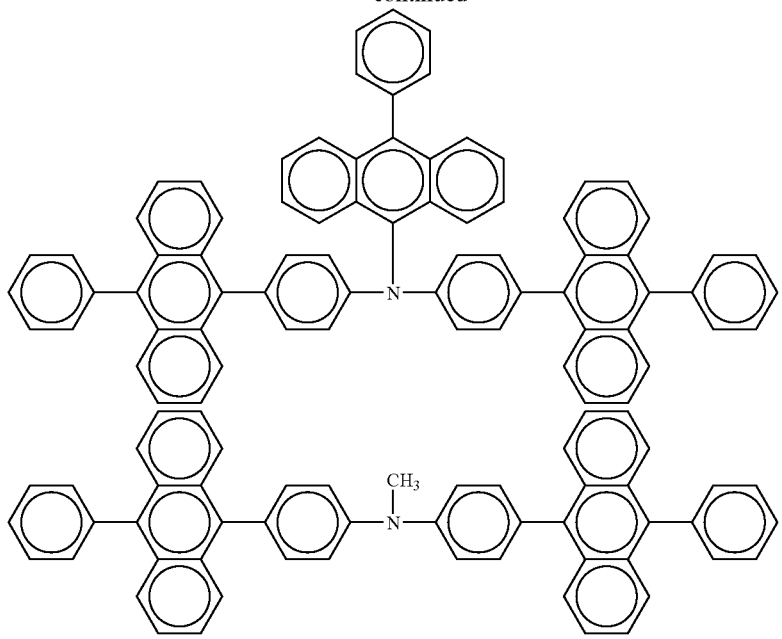
Naphthacene derivatives such as those mentioned below are also usable for light-emitting materials.
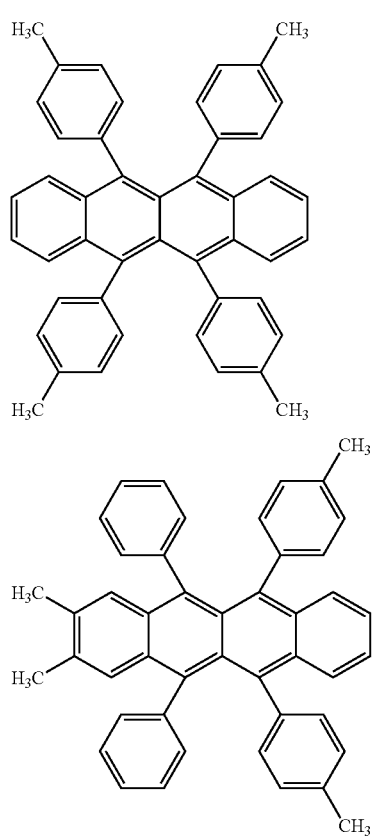
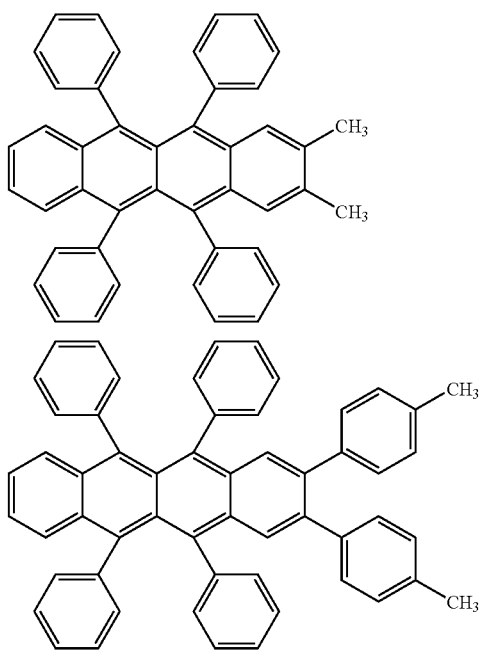

-continued

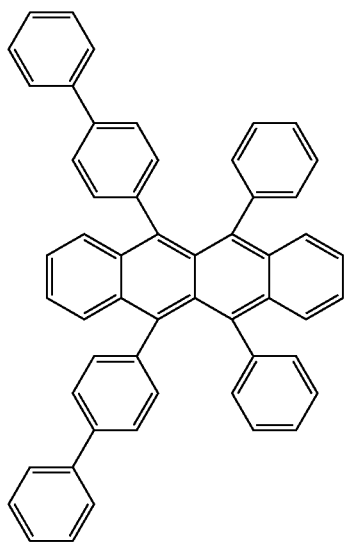

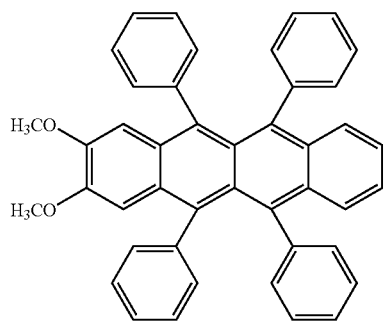

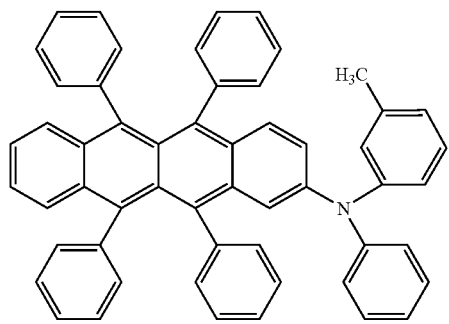

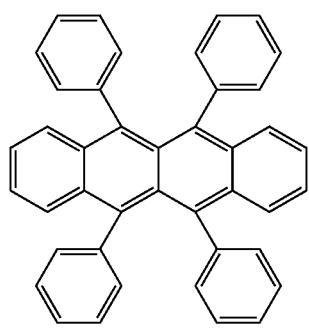

-continued

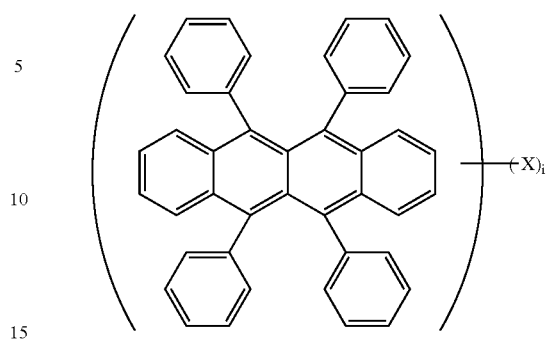

wherein X represents a cyano group, a substituted or unsubstituted alkyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, a substituted or unsubstituted cycloalkyl group, a substituted or unsubstituted heterocyclic group, a substituted or unsubstituted amino group, or a substituent for rubrene derivatives; i indicates an integer of from 1 to 28; and X's may be the same or different.

Amine compounds such as those mentioned below are also usable for light-emitting materials.

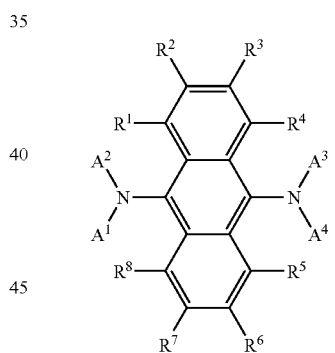

wherein $A^1$ to $A^4$ each independently represent an aryl group having from 6 to 16 carbon atoms; and $R^1$ to $R^8$ each independently represent a hydrogen atom, an alkyl group, an alkoxy group, an aryl group or an amino group.

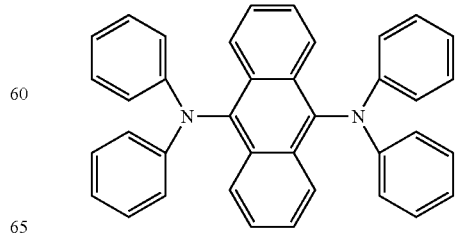

-continued
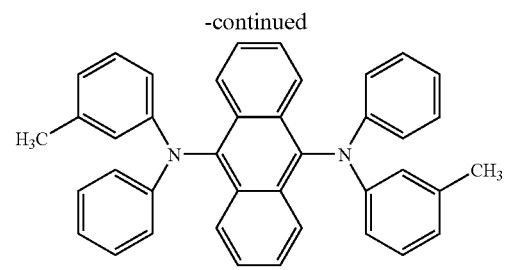
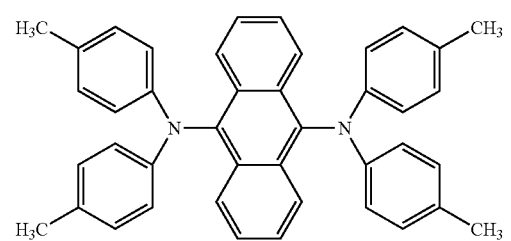
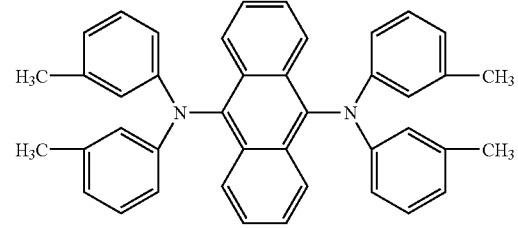
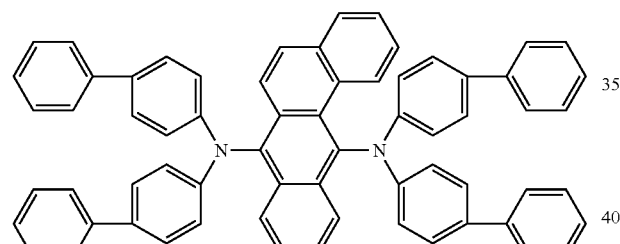
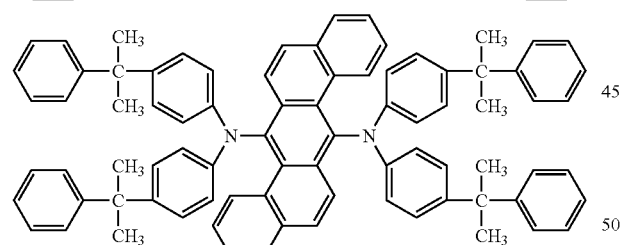
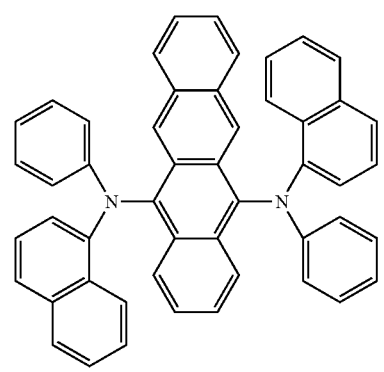
-continued
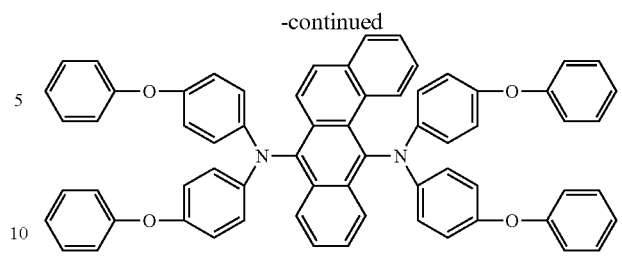
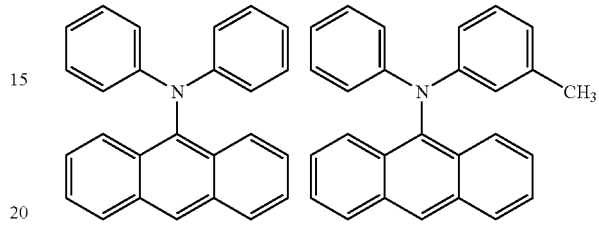
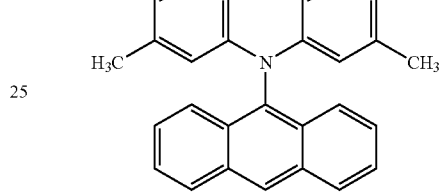
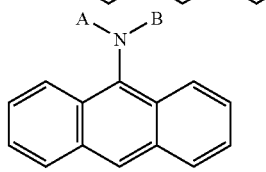
wherein A and B each represent an optionally-substituted aromatic ring.
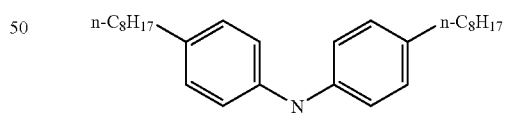
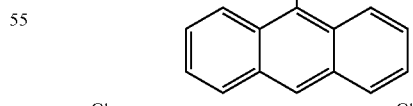
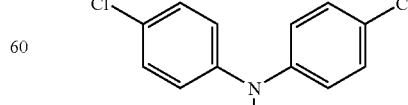
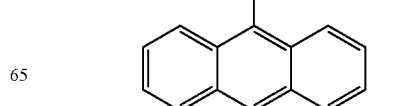

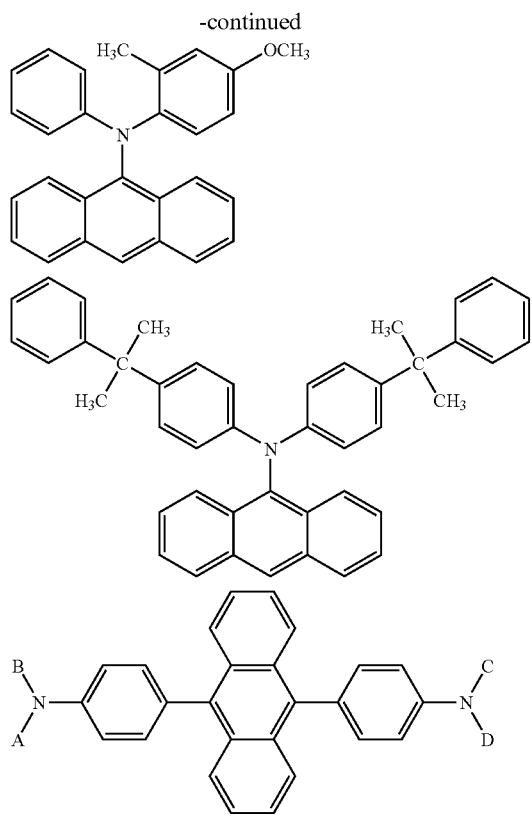

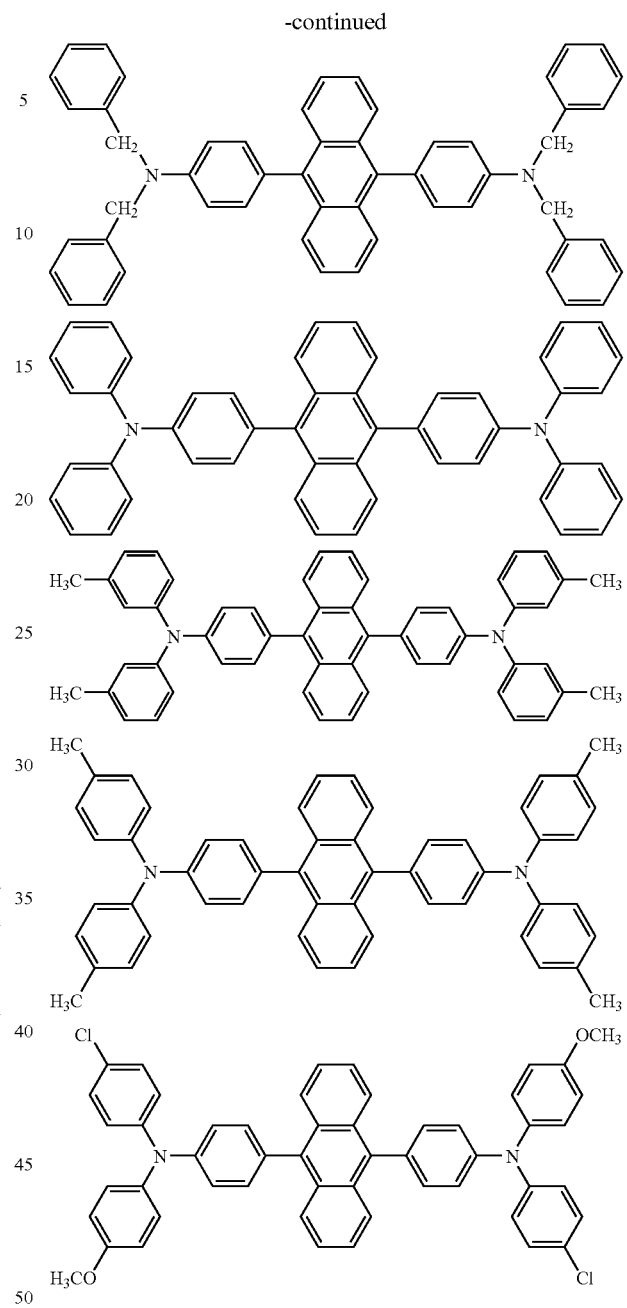

wherein A, B, C and D each represent a substituted or unsubstituted alkyl group, a substituted or unsubstituted monocyclic group, or a substituted or unsubstituted, condensed polycyclic group; and A and B, or C and B may together form a heterocyclic group along with the nitrogen atom that bonds to the skeleton.

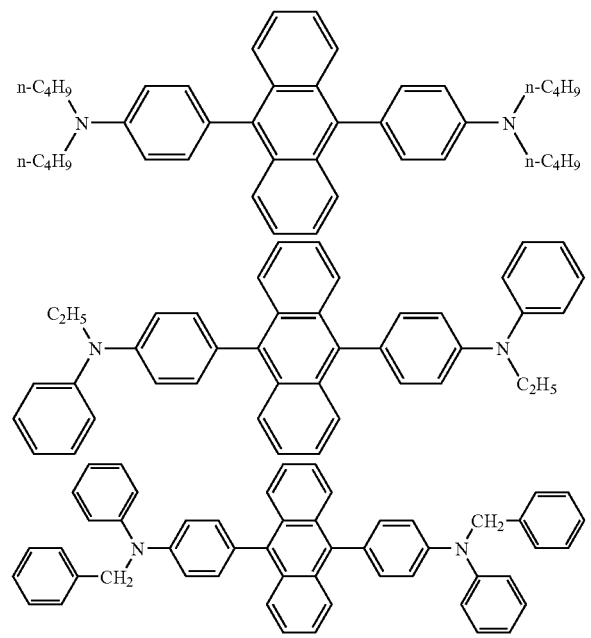

Other amine compounds also usable for light-emitting materials are mentioned below.

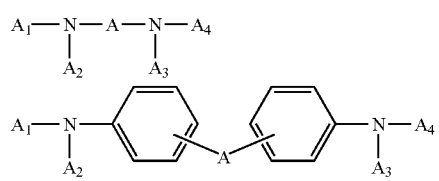

wherein $A^1$ to $A^4$ each independently represent an aryl group having from 6 to 16 carbon atoms, and the aryl group may be substituted with a hydrogen atom, an alkyl group, an alkoxy group, an aryl group or an amino group; and A represents a single bond, or an optionally-substituted arylene or polyarylene group.

Aromatic dimethylidene compounds (such as those described in European Patent 0388768 and Japanese Patent Laid-Open No. 231970/1991) are also usable for materials for emitting layers. In general, they are represented by the following formula:

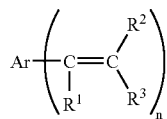

wherein Ar represents an arylene or polyarylene group; $R^1$ to $R^3$ each represent a hydrogen atom, an alkyl group or an aryl group; and n indicates an integer of from 1 to 6.

The aryl group includes a phenyl group, a biphenyl group, a terphenyl group, a naphthyl group, an anthryl group, a phenanthryl group, a pyrenyl group, a chrysenyl group, a fluorenyl group, etc. The arylene group includes a phenylene group, a biphenylene group, a terphenylene group, a naphthylene group, an anthrylene group, a phenanthrylene group, a pyrenylene group, a chrysenylene group, a fluorenylene group, etc. Preferably, the arylene group contains an anthracene skeleton, including, for example, an anthrylene group, a diphenylanthrylene group, a bianthrylene group, etc. $R^1$ is preferably a hydrogen atom. Specific examples of the compounds are 4,4'-bis(2,2-di-t-butylphenylvinyl)biphenyl,

---

4,4'-bis(2,2-diphenylvinyl)biphenyl, 4,4''-bis(2,2-diphenylvinyl)-p-terphenyl, 9,10-bis(4'-(2,2-diphenylvinyl)biphenyl)anthracene, 9,10-(4-(2,2-diphenylvinyl)phenyl)anthracene, 9,9'-(4-(2,2-diphenylvinyl)phenyl)-10,10'-bianthracene, and their derivatives.

---

In addition to the above, also usable herein are styryl group-having light-emitting materials. For these, preferred are styrylamine compounds of the following formula:

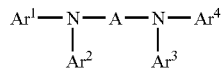

wherein $Ar^1$ to $Ar^4$ each represent an aryl group, and at least one of these is substituted with the following styryl group:

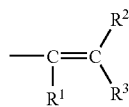

where $R^1$ to $R^3$ each represent a hydrogen atom, an alkyl group, or an aryl group.

The aryl group for $Ar^1$ to $Ar^4$ and $R^1$ to $R^3$ includes a phenyl group, a biphenyl group, a terphenyl group, a naphthyl group, an anthryl group, a phenanthryl group, a pyrenyl group, a chrysenyl group, a fluorenyl group, etc. $R^1$ is preferably a hydrogen atom. A indicates a linking group, representing a single bond, an arylene group or a polyarylene group. It includes a phenylene group, a biphenylene group, an anthrylene group, a phenanthrylene group, a pyrenylene group, a chrysenylene group, a diphenylanthrylene group, and also groups having any of the following structural formulae:

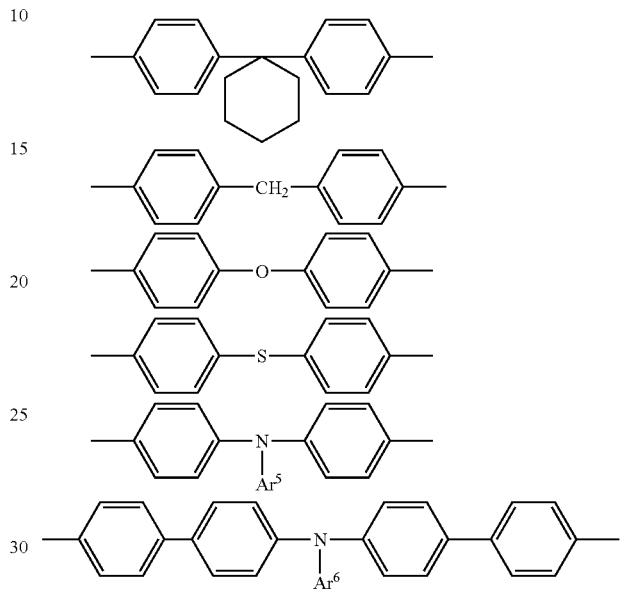

wherein $Ar^5$ and $Ar^6$ each represent an aryl group, like $Ar^1$ to $Ar^4$.

Also usable herein for light-emitting materials are compounds of a general formula, $(Rs-Q)_2-Al—O-L$ wherein L represents a hydrocarbon group containing a phenyl skeleton and having from 6 to 24 carbon atoms; O-L indicates a phenolato ligand; Q represents a substituted 8-quinolinolato ligand; Rs represents a specifically-selected substituent to be on the 8-quinolinolato ring, and it stereospecifically governs the structure of the compounds so that more than two substituted 8-quinolinolato ligands do not bond to the aluminium atom. The compounds are described in Japanese Patent Laid-Open No. 258862/1993. Concretely, they include bis(2-methyl-8-quinolinolato)(para-phenylphenolato)aluminium(III), bis(2-methyl-8-quinolinolato)(1-naphtholato)aluminium(III), etc.

In addition to the above, also employable herein is a doping method for efficient mixed emission of blue and green, as in Japanese Patent Laid-Open No. 9953/1994, etc. In the method, the host is any of the above-mentioned light-emitting materials, and the dopant is a fluorescent dye of high blue to green emission. For example, the dopant is a coumarin dye or any other fluorescent dye that may be selected from fluorescent dyes serving as the host. Concretely, the host is a light-emitting material having a distyrylarylene skeleton, preferably 4,4'-bis(2,2-diphenylvinyl)biphenyl, and the dopant is a diphenylaminovinylarylene, preferably N,N-diphenylaminovinylbenzene.

The emitting layer for white emission is not specifically defined, and may be any of the following:

<1> A layer that defines the energy level of the layers constituting a multi-layered organic EL structure, and emits light through tunnel injection thereinto (European Patent 0390551);

<2> A layer that emits light through tunnel injection thereinto, like <1> (Japanese Patent Laid-Open No. 230584/1991—its Examples demonstrate white-emitting devices);

<3> A two-layered emitting layer (Japanese Patent Laid-Open Nos. 220390/1990 and 216790/1990);

<4> A layer partitioned into a plurality of sections, in which the light-emitting materials for the respective sections differ in the wavelength range within which they emit light (Japanese Patent Laid-Open No. 51491/1992);

<5> A stacked layer composed of a blue-emitting layer. (having a fluorescent peak that falls between 380 and 480 nm) and a green-emitting layer (having a fluorescent peak that falls between 480 and 580 nm), and further containing a red-emitting fluorescent material (Japanese Patent Laid-Open No. 207170/1994);

<6> A combination of a blue-emitting layer that contains a blue-emitting fluorescent dye and a green-emitting layer that contains a red-emitting fluorescent dye, which further contains a green-emitting fluorescent material (Japanese Patent Laid-Open No. 142169/1995).

Of these, especially preferred is the structure <5>.

For the red-emitting fluorescent material, preferred are the following compounds:

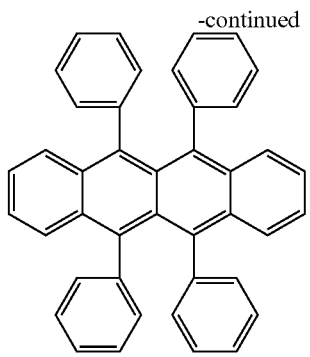
-continued

Next described is a method for forming an emitting layer from any of the materials mentioned above. Any known methods are applicable to emitting layer formation, including, for example, vapor deposition, spin coating, LB film formation, etc. For the emitting layer, especially preferred is a molecular deposition film. The molecular deposition film referred to herein is a thin film formed through vapor deposition of a material compound of being in a vapor phase condition, or a film formed through solidification of a material compound of being in a solution condition or in a liquid phase condition. In general, the molecular deposition film of that type could be differentiated from a thin film (molecular built-up film) formed in a method of LB film formation, because of the difference therebetween in the aggregation structure and the high-order structure and of the functional difference therebetween resulting from it.

Another method is employable for forming the emitting layer, which comprises dissolving a material compound in a solvent along with a binder such as resin or the like to prepare a solution, followed by filming the resulting solution into a thin film through spin coating or the like, as in Japanese Patent Laid-Open No. 51781/1982.

The thickness of the emitting layer thus formed in the manner mentioned above is not specifically defined. Depending on the condition, the thickness of the layer may be suitably varied, but preferably falls between 5 nm and 5 µm. The emitting layer may have a single-layered structure comprising one or more of the materials mentioned above, or may have a multi-layered structure having additional emitting layer(s) of different compound(s).

Next described is the hole injection/transporting layer to be in the organic EL device of the invention. The layer is to assist hole injection into the emitting layer, transporting holes to the emitting region of the emitting layer. Its hole mobility is high, but its ionization energy is small, generally at most 5.5 eV. For the hole injection/transporting layer, preferred is a material capable of transporting holes to the emitting layer at a lower field strength. More preferably, the hole mobility in the layer is at least $10^{-6}$ cm$^2$/V·sec, for example, in an electric field falling between $10^4$ and $10^6$ V/cm. The material mixed with an aromatic hydrocarbon compound for use herein to form the hole injection/transporting layer is not specifically defined, so far as the layer formed could have the preferred properties mentioned above. The material for the layer may be selected from any conventional photoconductive materials ordinarily used for hole-transporting materials, and also from any known materials ordinarily used for hole injection layers in organic EL devices.

Concretely, the material for forming the hole injection/transporting layer includes, for example, triazole derivatives (see U.S. Pat. No. 3,112,197, etc.), oxadiazole derivatives (see U.S. Pat. No. 3,189,447, etc.), imidazole derivatives (see Japanese Patent Publication No. 16096/1962, etc.), polyarylalkane derivatives (see U.S. Pat. Nos. 3,615,402, 3,820,989, 3,542,544, Japanese Patent Publication Nos. 555/1970, 10983/1976, Japanese Patent Laid-Open Nos. 93224/1976, 17105/1980, 4148/1981, 108667/1980, 156953/1980, 36656/1981, etc.), pyrazoline derivatives and pyrazolone derivatives (see U.S. Pat. Nos. 3,180,729, 4,278,746, Japanese Patent Laid-Open Nos. 88064/1980, 88065/1980, 105537/1974, 51086/1980, 80051/1981, 88141/1981, 45545/1982, 112637/1979, 74546/1980, etc.), phenylenediamine derivatives (see U.S. Pat. No. 3,615,404, Japanese Patent Publication Nos. 10105/1976, 3712/1971, 25336/1972, Japanese Patent Laid-Open Nos. 53435/1979, 110536/1979, 119925/1979, etc.), arylamine derivatives (see U.S. Pat. Nos. 3,567,450, 3,180,703, 3,240,597, 3,658,520, 4,232,103, 4,175,961, 4,012,376, Japanese Patent Publication Nos. 35702/1974, 27577/1964, Japanese Patent Laid-Open Nos. 144250/1980, 119132/1981, 22437/1981, German Patent 1,110,518, etc.), amino-substituted chalcone derivatives (see U.S. Pat. No. 3,526,501, etc.), oxazole derivatives (such as those described in U.S. Pat. No. 3,257,203, etc.), styrylanthracene derivatives (see Japanese Patent Laid-Open No. 46234/1981, etc.), fluorenone derivatives (see Japanese Patent Laid-Open No. 110837/1979, etc.), hydrazone derivatives (see U.S. Pat. No. 3,717,462, Japanese Patent Laid-Open Nos. 59143/1979, 52063/1980, 52064/1980, 46760/1980, 85495/1980, 11350/1982, 148749/1982, 311591/1990, etc.), stilbene derivatives (see Japanese Patent Laid-Open Nos. 210363/1986, 228451/1986, 14642/1986, 72255/1986, 47646/1987, 36674/1987, 10652/1987, 30255/1987, 93455/1985, 94462/1985, 174749/1985, 175052/1985, etc.), silazane derivatives (see U.S. Pat. No. 4,950,950), polysilane derivatives (see Japanese Patent Laid-Open No. 204996/1990), aniline-based copolymers (see Japanese Patent Laid-Open No. 282263/1990), electroconductive high-molecular weight oligomers (especially thiophene oligomers) described in Japanese Patent Laid-Open No. 211399/1989, etc.

For the materials for the hole injection/transporting layer, usable are those mentioned above. In addition, also usable are porphyrin compounds (such as those described in Japanese Patent Laid-Open No. 295695/1988, etc.), aromatic tertiary amine compounds and styrylamine compounds (see U.S. Pat. No. 4,127,412, Japanese Patent Laid-Open Nos. 27033/1978, 58445/1979, 149634/1979, 64299/1979, 79450/1980, 144250/1980, 119132/1981, 295558/1986, 98353/1986, 295695/1988, etc.), and other aromatic tertiary amine compounds.

Further usable are compounds having two condensed aromatic rings in the molecule such as those described in U.S. Pat. No. 5,061,569, e.g., 4,4'-bis(N-(1-naphthyl)-N-phenylamino)biphenyl; 4,4',4''-tris(N-(3-methylphenyl)-N-phenylamino)triphenylamine with three triphenylamine units being starburst-wise bonded to the center nitrogen atom, such as that described in Japanese Patent Laid-Open No. 308688/1992, etc. In addition, the aromatic dimethylidene compounds mentioned hereinabove for the materials for the emitting layer, and inorganic compounds such as p-type Si, p-type SiC and others are also usable for the materials for the hole injection/transporting layer.

For forming the hole injection/transporting layer, any of the compounds mentioned above is filmed into a thin film in any known method of, for example, vacuum evaporation, spin coating, casting, LB film formation, etc. The thickness of the hole injection/transporting layer is not specifically defined, generally falling between 5 nm and 5 μm. If containing an aromatic hydrocarbon compound for use herein in its hole transporting zone, the hole injection/transporting layer may have a single-layered structure comprising one or more of the materials mentioned above, or may have a multi-layered structure having additional hole injection/transporting layer(s) of different compound(s).

Next described is the organic semiconductor layer. This is to assist hole injection or electron injection into the emitting layer, and preferably has en electroconductivity of at least $10^{-10}$ S/cm. Examples of the material for the organic semiconductor layer are electroconductive oligomers such as thiophene-containing oligomers, arylamine-containing oligomers described in Japanese Patent Laid-Open No. 193191/1996, etc.; electroconductive dendrimers such as arylamine-containing dendrimers, etc.

Next described is the electron injection layer. This is to assist electron injection into the emitting layer, and has high electron mobility. When formed from a material of good adhesion to cathodes, the electron injection layer serves also as an adhesion improving layer. For the materials for the electron injection layer, preferred are metal complexes of 8-hydroxyquinoline or its derivatives. Specific examples of metal complexes of 8-hydroxyquinoline or its derivatives that serve as electron-injecting materials for use herein are metal-chelated oxinoid compounds having an oxine (generally 8-quinolinol or 8-hydroxyquinoline) chelate, such as tris(8-quinolinol)aluminium.

Oxadiazole derivatives that serve as electron-transmitting compounds are also usable herein. Typically, they are represented by any of the following general formulae [4] to [6]:

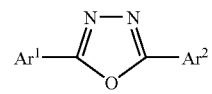

[4]

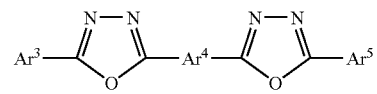

[5]

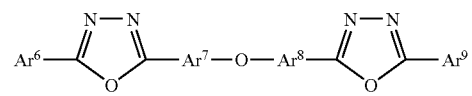

[6]

wherein $Ar^1$, $Ar^2$, $Ar^3$, $Ar^5$, $Ar^6$ and $Ar^9$ each independently represent a substituted or unsubstituted aryl group, and these may be the same or different; $Ar^4$, $Ar^7$ and $Ar^8$ each independently represent a substituted or unsubstituted arylene group, and these may be the same or different.

The aryl group in these formulae [4] to [6] includes a phenyl group, a biphenyl group, an anthranyl group, a perylenyl group, a pyrenyl group. The arylene group therein includes a phenylene group, a naphthylene group, a biphenylene group, an anthranylene group, a perylenylene group, a pyrenylene group, etc. The substituents for these groups include an alkyl group having from 1 to 10 carbon atoms, an alkoxy group having from 1 to 10 carbon atoms, a cyano group, etc. Of the electron-transmitting compounds, preferred are those capable of being readily filmed into thin films.

Specific examples of the electron-transmitting compounds are mentioned below.

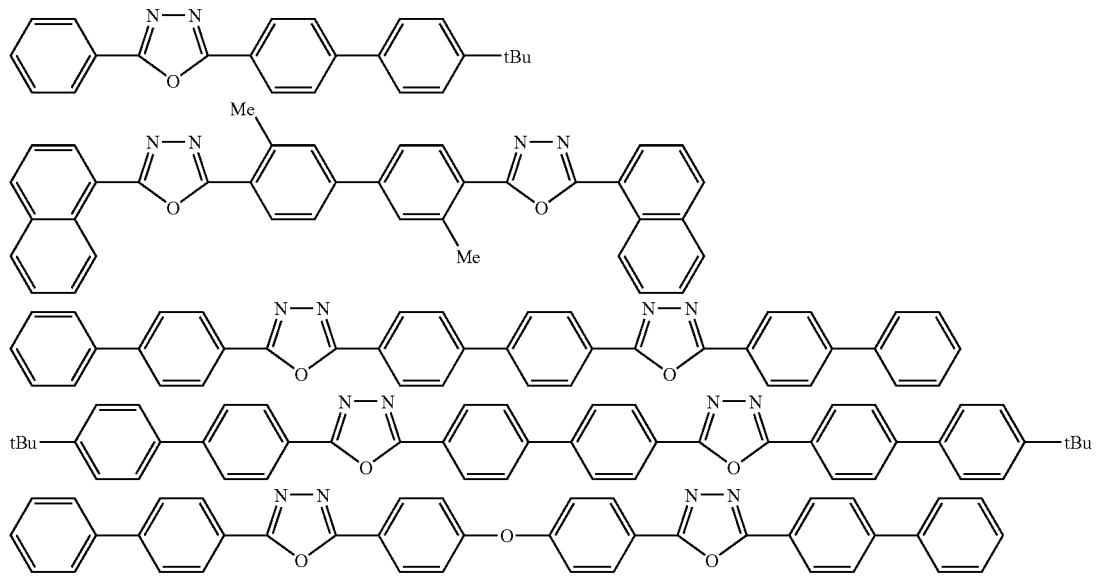

Next described is the cathode. For the electrode material for the cathode, usable are metals, alloys, electroconductive compounds and their mixtures having a small work function (at most 4 eV). Specific examples of the electrode material are sodium, sodium-potassium alloys, magnesium, lithium, magnesium-silver alloys, aluminium/aluminium oxide, aluminium-lithium alloys, indium, rare earth metals, etc.

To form the cathode, the electrode material is formed into a thin film through vapor deposition, sputtering or the like.

In case where the light from the emitting layer is taken out through the cathode, it is desirable that the cathode has a light transmittance of larger than 10%. Also preferably, the sheet resistance of the cathode is at most hundreds Ω/square. The thickness of the cathode generally falls between 10 nm and 1 μm, but preferably between 50 nm and 200 nm.

Next described is a method for fabricating the organic EL device of the invention. Using the materials mentioned above and according to the processes also mentioned above, an anode, an emitting layer, and optionally a hole injection layer, and further optionally an electron injection layer are formed in that order, and a cathode is finally formed. Opposite to this order, a cathode is first formed and an anode is formed last to finish the organic EL device of the invention.

Described hereinunder is one embodiment of fabricating the organic EL device of the invention which has a structure of anode/hole injection layer/emitting layer/electron injection layer/cathode formed on a transparent substrate in that order.

A thin film of an anode material having a thickness of at most 1 μm, preferably from 10 to 200 nm is first formed on a suitable transparent substrate through vapor deposition or sputtering. This serves as an anode. Next, a hole injection layer is formed on the anode. To form it, employable is any of vacuum evaporation, spin coating, casting, LB film formation or the like as so mentioned hereinabove, but preferred is vacuum evaporation as ensuring homogeneous films with few pin holes. In case where the hole injection layer is formed through vacuum evaporation, the condition for vapor deposition varies, depending on the compound used (for the material for the hole injection layer), and on the crystal structure and the recombination structure of the hole injection layer to be formed. In general, it is desirable that the temperature of the vapor source falls between 50 and 450° C., the vacuum degree falls between $10^{-7}$ and $10^{-3}$ Torr, the deposition rate falls between 0.01 and 50 nm/sec; the substrate temperature falls between −50 and 300° C., the thickness of the film formed falls between 5 nm and 5 μm.

Next, an emitting layer is formed on the hole injection layer. For forming it, a desired organic light-emitting material is filmed into a thin film through vacuum evaporation, sputtering, spin coating, casting or the like. Preferred is vacuum evaporation as ensuring homogeneous films with few pin holes. In case where the emitting layer is formed through vacuum evaporation, the condition for vapor deposition varies, depending on the compound used. In general, the condition for hole injection layer formation mentioned above could apply also to the emitting layer formation.

Next, an electron injection layer is formed on the emitting layer. Like the hole injection layer and the emitting layer, the electron injection layer must also be made of a homogeneous film, for which, therefore, preferred is vacuum evaporation. The condition for vapor deposition to form the electron injection layer may also be similar to that to form the hole injection layer and the emitting layer.

Finally, a cathode is formed on the electron injection layer to finish the intended organic EL device. The cathode is formed from a metal, for which is employable vapor deposition or sputtering. However, in order not to damage the underlying organic layers, preferred is vacuum evaporation.

The process of fabricating the organic EL device mentioned above is preferably achieved in one and the same vacuum chamber in which the degree of vacuum is not changed throughout the process of forming all the layers, from the anode to the cathode.

In case where a direct current voltage is applied to the organic EL device thus produced in the manner as above, a voltage of from 5 to 40 V may be applied thereto with its anode being charged to be plus (+) and its cathode to be minus (−), whereby the device emits light. Even if the same voltage is applied to the device in the reversed manner relative to the polarity of the electrodes, the device emits no light. On the other hand, in case where an alternating current is applied to the device, the device emits light only when its anode is charged to be plus (+) and its cathode to be minus (−). The wave mode of the alternating current to be applied to the device may be any desired one.

In the invention, at least one, but preferably at least two organic compounds for forming the organic compound layers of the organic EL device having the constitution as above have an impurity concentration of lower than 1000 ppm. In that condition, the organic compounds layers of the device are formed. More preferably, all the organic compound layers of the device have an impurity concentration of lower than 1000 ppm.

Purification to prepare such high-purity organic compounds is not specifically defined, and may be effected through sublimation, recrystallization, re-precipitation, zone melting, column purification, adsorption or the like. If desired, these purification methods may be combined in any desired manner. Of those, preferred is recrystallization for obtaining the intended high-purity organic compounds. For purifying sublimable compounds, preferred is sublimation. For purifying sublimable compounds through sublimation, it is desirable that the sublimation boat is first kept at a temperature lower than the sublimation point of the compound to be purified so as to previously remove the sublimable impurities from the compound before the compound is sublimed. Also preferably, the zone in which the sublimed compound is collected is designed to have a temperature gradient therethrough so that the sublimed mixture could be fractionated into the intended product and the impurities. The sublimation purification mode mentioned above is for purifying a compound by removing impurities from it, and is applicable to the invention.

Also preferably, organic compounds in which the oxygen and nitrogen atoms are directly or indirectly bonded to the π-conjugated carbon-carbon main chain (these are referred to as chelate complex compounds) are purified through sublimation. For sublimation purification, known are a stirring method and a shaking method. The stirring method includes (A) a mechanical stirring method in which lumps of an aggregated organic compound are directly crushed and milled with a man-powered or machine-powered stirring blade fitted to the tip of a stirrer sealed in vacuum, and stirring the system is continued so that the milled power is prevented from again aggregating to form lumps; (B) a magnetic stirring method in which is used a magnetic bar for milling an organic compound to be purified through sublimation in such a manner that the magnetic bar is rotated at a desired speed of rotation by the use of an external rotating machine to thereby directly crush and mill the lumps of the organic compound, and stirring the system is continued so that the milled power is prevented from again aggregating to form lumps; and (C) a method of dropping metal balls such as iron balls or the like onto the lumps of an organic compound to thereby directly crush and mill the lumps. Any of these methods is employable herein.

The shaking method includes (a) an ultrasonic shaking method in which an organic compound to be purified through sublimation is put into a container and exposed to ultrasonic waves from an external ultrasonic wave generator, thereby crushing and milling the lumps of the organic compound; and (b) a direct shaking method in which an organic compound to be purified through sublimation is put into a container, and the container is directly shaken by an external shaking machine fitted to the container or by human power applied thereto to thereby crush and mill the lumps of the organic compound. Any of these methods is employable herein.

The organic compound of which the impurity content has been reduced to smaller than 1000 ppm in the manner mentioned above is used for forming at least one organic compound layer of the organic EL device of the invention.

The impurities that may be in the organic compound materials to be formed into the organic compound layers of the device of the invention are generally derived from the starting substances used for preparing the organic compound materials, further including intermediates and precursors produced in the process of preparing the organic compounds (some intermediates and precursors produced in the process often have a reactive functional group). In addition, in case where halogen compounds are used in the process of preparing the organic compounds, unreacted intermediates will remain in the reaction system, and the starting halogen compounds not reacted completely will also remain therein. These unreacted intermediates and halogen compounds will be impurities in the organic compounds prepared. Moreover, in case where halogen solvents are used in the process of preparing the organic compounds, the organic compounds prepared will be often contaminated by halogen (e.g., chlorine)-added olefins, or, depending on the reaction condition, by oxidized organic compounds.

Accordingly, the organic compound materials are, immediately after having been prepared through chemical synthesis, often contaminated by impurities of various compounds. Of all such impurities, we, the present inventors have found that halogen compounds are the most serious, as significantly attenuating emission luminance and shortening the emission life. Many impurities mentioned above contain halogen atoms acting as a reactive functional group, and they trap holes and electrons that have moved from the electrodes into the organic compound layers. Accordingly, the acceptable uppermost limit of the halogen-containing impurities that may be in the organic compound materials is 500 ppm. We have found that organic EL devices in which the organic compound layers are formed from materials having a halogen compound content higher than the uppermost limit are often significantly confronted with the problems of emission luminance attenuation and short emission life.

Just after having been prepared through chemical synthesis, organic compound materials are often contaminated with impurities, which are described more concretely. For example, in chemical synthesis of producing styryl compounds to be represented by the following reaction formula:

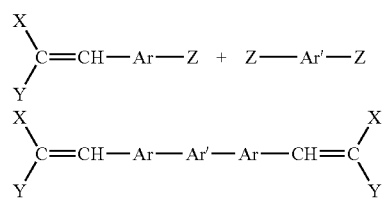

wherein Ar, Ar', X and Y each represent an aryl group; and Z represents a halogen atom, halogen compounds of the following formulae:

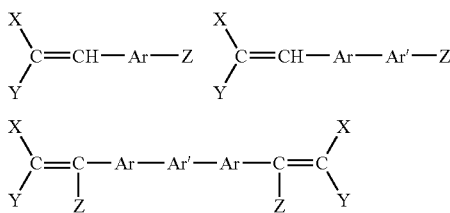

wherein Ar, Ar', X and Y each represent an aryl group; and Z represents a halogen atom.

exist as impurities in the reaction system. Accordingly, organic compound materials comprising the styryl compounds prepared through the reaction mentioned above are contaminated with the impurities of such halogen compounds.

In chemical synthesis of producing amine compounds to be represented by the following reaction formula:

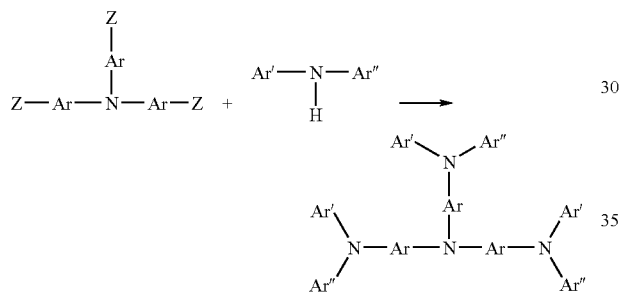

wherein Ar, Ar' and Ar" each represent an aryl group; and Z represents a halogen atom, halogen compounds of the following formulae:

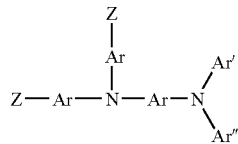

wherein Ar, Ar' and Ar" each represent an aryl group; and Z represents a halogen atom, and also amine oxides exist as impurities in the reaction system. Accordingly, organic compound materials comprising the amine compounds prepared through the reaction mentioned above are contaminated with the impurities of such halogen compounds and amine oxides. These are examples of intermediates and precursors in the process of chemical synthesis.

Amine compounds may be prepared through the following reaction, which also gives some impurities to be mentioned below.

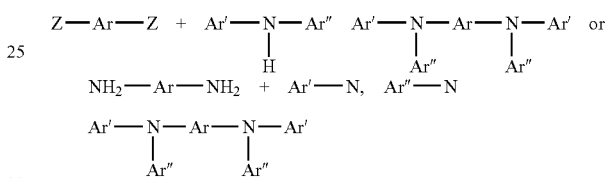

In these processes, the products produced will be contaminated with the following impurities, intermediates or precursors.

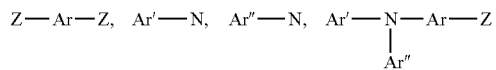

wherein Ar, Ar' and Ar" each represent an aryl group; and Z represents a halogen atom.

Polyfluorenone compounds will be contaminated with the following impurities:

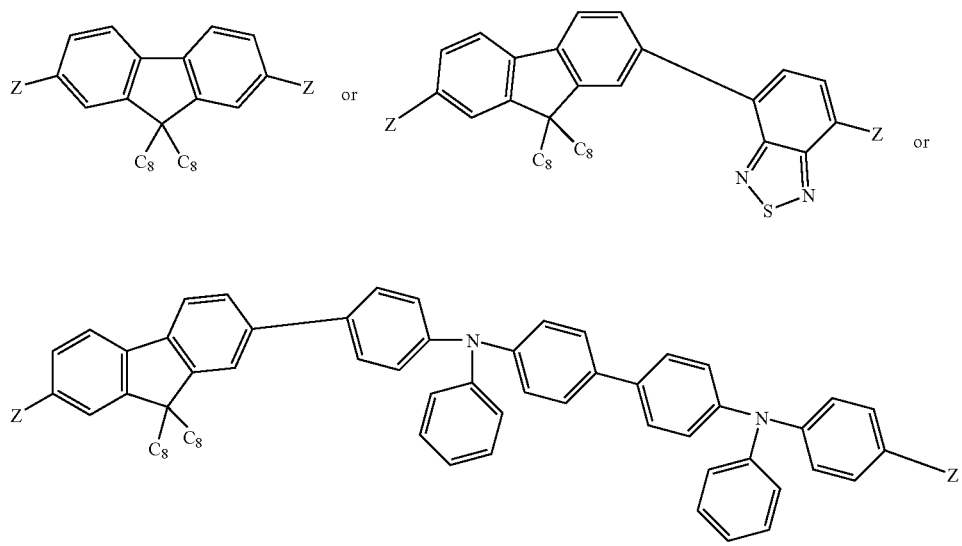

wherein Z represents a halogen atom.

In case where various organic compounds for use herein are produced in other processes of chemical reaction, the organic compounds produced should be so controlled that their impurity content is smaller than 1000 ppm, including 0 ppm. The impurities of the organic compounds may be derived from the starting substances used, or may be intermediates or precursors formed in the process of chemical reaction to give the organic compounds, or may be such intermediates or precursors having a reactive functional group (including, for example, halogens, amino, hydroxy and carboxyl groups, etc.).

Various methods are known for quantifying the impurity content of the organic compound materials purified in various purification methods such as those mentioned above. In the invention, the purified organic compound materials are analyzed through high-performance liquid chromatography to quantify the impurities therein, and those of which the impurity content is lower than the predetermined value as above are selectively used for forming the organic compound layers of the organic EL device of the invention. For selecting the organic compound materials for use herein, high-performance liquid chromatography is preferred to any other methods. This is because organic compound materials suitable to the invention are selected more rapidly and more accurately in the method of high-performance liquid chromatography than in any other methods.

In the method of high-performance liquid chromatography, the mobile phase is moved in the column by the power of a high-pressure pump (pressure: 350 to 500 kg/cm$^2$). In the method, therefore, the time for separation is short, and rapid quantification is possible. The filler for the method comprises porous particles all having a small grain size of from 5 to 10µ and having a large surface area, and therefore has good separation capability. The column can be connected with a high-sensitivity detector, in which accurate analysis is possible. In addition, since the flow rate through the column can be kept constant all the time, the method of high-performance liquid chromatography ensures good reproducibility. Some typical examples of the filler and the separation mode for the method of high-performance liquid chromatography are shown in Table 1.

TABLE 1

| Separation Mode | Parameter for Separation | Typical Filler |
|---|---|---|
| Partitioning Chromatography | Solubility | Chemical-bonding silica gel, Polymer gel, Carbon, Chemical-bonding porous glass |
| Adsorption Chromatography | Adsorbability | Silica gel, Alumina, Porous glass, Carbon |
| Ion-exchange Chromatography | Ion-exchangeability | Ion-exchangeable polystyrene gel, Ion-exchangeable chemical-bonding silica gel, Ion-exchangeable hydrophilic polymer gel |
| Sizing Chromatography | Molecular size | Polystyrene gel, Hydrophilic polymer gel, Chemical-bonding silica gel |
| Affinity | Biochemical affinity | Ligand-bonding |

TABLE 1-continued

| Separation Mode | Parameter for Separation | Typical Filler |
|---|---|---|
| Chromatography | | hydrophilic polymer, Ligand-bonding silica gel |

In the method of high-performance liquid chromatography, the separation mode varies, depending on the fixed phase and the mobile phase, and may be any desired one.

For quantifying the impurities in the organic compound materials to be used herein for forming organic compound layers of the organic EL device of the invention, preferred is reversed-phase chromatography as its separation efficiency is good. Reversed-phase chromatography is a type of partitioning chromatography, and the filler used therein is ODS (octadecyl-bonding silica) which is a type of chemical-bonding silica gel. Such an ODS filler is a typical one for high-performance liquid chromatography, and is applicable to a broad range of various compounds. The solvent for reversed-phase chromatography may be a polar solvent including methanol, acetonitrile and others, or may also be a mixed solvent of water and such a polar solvent. Especially preferred is acetonitrile.

Any detector is usable in high-performance liquid chromatography, including, for example, an ultraviolet absorptiometer (UV), a differential refractometer (RI), etc. Preferred is an ultraviolet absorptiometer (UV), since the base line for the data detected therein is stable, and the data are not influenced by the ambient temperature and the flow rate, therefore ensuring high-sensitivity detection.

Accordingly, the best combination of the filler, the solvent and the detector for high-performance liquid chromatography to be employed herein is as follows. The filler is ODS; the solvent is acetonitrile for reversed-phase chromatography; and the detector is an ultraviolet absorptiometer (UV).

In case where the organic compound materials to be used for forming the layers of the organic EL device of the invention are soluble in the solvent, acetonitrile, there occurs no problem in analyzing the materials through high-performance liquid chromatography with the solvent, acetonitrile. However, in case where the materials are hardly soluble in the solvent, acetonitrile, they must be processed as follows: The material to be analyzed is first dissolved in a solvent capable of dissolving it, and then a bad solvent, for example, methanol or a mixed solvent of methanol and water is added to the resulting solution for re-precipitating it. Next, the insoluble solid is taken out through filtration, and the solvent is completely evaporated away by the use of an evaporator. Acetonitrile is added to this to prepare a sample solution of the material in acetonitrile. In that manner, the organic compound materials hardly soluble in acetonitrile can be analyzed through high-performance liquid chromatography with acetonitrile.

Next, the invention is described in more detail with reference to the following Examples.

PRODUCTION EXAMPLE 1

Preparation of Hole Injection Material 4,4',4"-Tris-[N-(M-tolyl)-N-phenylamino]triphenylamine (hereinafter referred to as MTDATA) having the following formula is prepared in the manner mentioned below. This serves as a hole injection material.

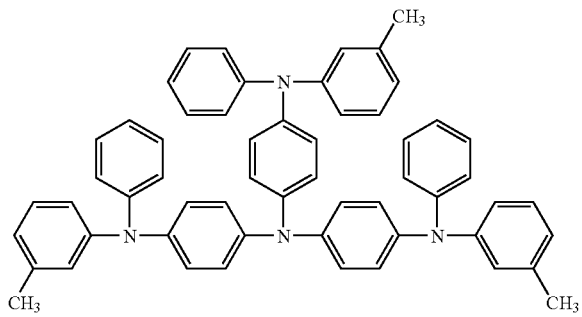

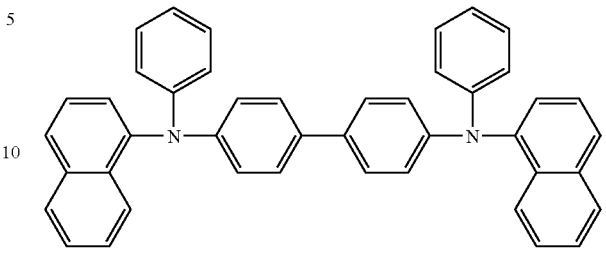

1.0 g of 4,4',4''-triiodotriphenylamine, 1.0 g of N-(3-tolyl)-N-phenylamine (from Aldrich), 3 g of anhydrous potassium carbonate and 1.0 g of copper powder were put into a 300-ml three-neck flask, to which was added 200 ml of dimethylsulfoxide to dissolve them. At 200° C., these were reacted for 8 hours with stirring. After having been reacted, the reaction mixture was filtered, and the mother filtrate was extracted with methylene chloride. Next, the solvent was evaporated away by the use of a rotary evaporator. The residue was subjected to column chromatography, for which the column was filled with silica gel and the developer was toluene. 0.3 g of a pale yellow powder was obtained. This is hereinafter referred to as impure MTDATA.

The impure MTDATA was analyzed through high-performance liquid chromatography. The impurities detected were N-(3-tolyl)-N-phenylamine, halogen-containing impurities such as triiodotriphenylamine derivatives, diiodotriphenylamine derivatives, monoiodotriphenylamine derivatives, and amine oxides. The amount of some these impurities fell between 1000 and 10000 ppm.

Next, the impure MTDATA was purified through sublimation to remove the impurities from it. The boat temperature was 390° C., and the vacuum degree was $10^{-6}$ Torr. As a result, obtained was 0.24 g of a pale yellow powder. This is hereinafter referred to as sublimed MTDATA. The sublimed MTDATA was analyzed through high-performance liquid chromatography, which confirmed that the amount of the above-mentioned impurities was all smaller than 1000 ppm.

PRODUCTION EXAMPLE 2

Preparation of Hole Transporting Material

N,N'-Di(naphthyl-1-yl)-N,N'-diphenyl-4,4'-benzidine (hereinafter referred to as NPD) having the following formula is prepared in the manner mentioned below. This serves as a hole transporting material.

2.0 g of 1-iodonaphthalene (from Tokyo Chemical), 1.0 g of N,N'-diphenylbenzidine (from Aldrich), 3 g of anhydrous potassium carbonate and 1.0 g of copper powder were put into a 300-ml three-neck flask, to which was added 200 ml of dimethylsulfoxide to dissolve them. At 200° C., these were reacted for 8 hours with stirring. After having been reacted, the reaction mixture was filtered, and the mother filtrate was extracted with methylene chloride. Next, the solvent was evaporated away by the use of a rotary evaporator. The residue was subjected to column chromatography, for which the column was filled with silica gel and the developer was toluene. 0.37 g of a pale yellow powder was obtained. This is hereinafter referred to as impure NPD.

The impure NPD was analyzed through high-performance liquid chromatography. The impurities detected were the halogen-containing non-reacted compound, 1-iodonaphthalene, and also N-(naphthyl-1-yl)-N,N'-diphenyl-4,4'-benzidine, and amine oxides. The amount of some these impurities fell between 1000 and 10000 ppm.

Next, the impure NPD was purified through sublimation to remove the impurities from it. The boat temperature was 320° C., and the vacuum degree was $10^{-6}$ Torr. As a result, obtained was 0.31 g of a pale yellow powder. This is hereinafter referred to as sublimed NPD. The sublimed NPD was analyzed through high-performance liquid chromatography, which confirmed that the amount of the above-mentioned impurities was all smaller than 1000 ppm.

PRODUCTION EXAMPLE 3

Preparation of Dopant 4,4'-Bis[2-{4-(N,N-diphenylamino)phenyl}vinyl]biphenyl (hereinafter referred to as DPAVBi) having the following formula is prepared in the manner mentioned below. This serves as a dopant.

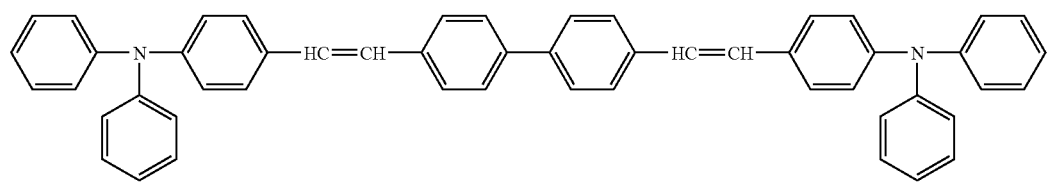

1.9 g of biphenyl phosphonate and 3.0 g of N,N-diphenyl-4-aminobenzaldehyde were put into a 200-ml three-neck flask, to which was added 50 ml of dimethylsulfoxide to dissolve them. Next, with stirring them in an argon atmosphere at room temperature with a magnetic stirrer, 1.0 g of powdery potassium t-butoxide (from Kanto Chemical) was added thereto little by little. The reaction mixture immediately became reddish black, and then faded to give a precipitate which was first greenish yellow and then ocher. The reaction mixture was further stirred at room temperature for 3 hours. This was left at room temperature overnight, and then 50 ml of aqueous 80 wt. % methanol solution was gradually added thereto. Then, the yellow precipitate formed was taken out through filtration, and then washed with water. Washing it was repeated a few times. An yellow powder was obtained, weighing 2.8 g.

The thus-obtained yellow powder was purified through silica gel column chromatography, for which the developer was toluene, and then recrystallized from toluene. Recrystallizing it was repeated a few times. An yellow powder was obtained, weighing 1.6 g.

The product thus obtained was analyzed through high-performance liquid chromatography. The impurities detected were 4-(N,N-diphenyl)-4'-(p-tolyl)stilbene and amine oxides, but were all smaller than 1000 ppm.

PRODUCTION EXAMPLE 4

Preparation of Light-emitting Material 4,4"-Bis(2,2-diphenylvinyl)-p-terphenyl (hereinafter referred to as DPVTP) having the following formula is prepared in the manner mentioned below. This serves as a light-emitting material.

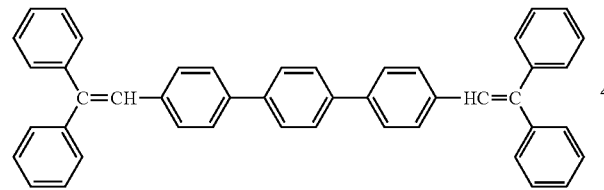

200 g of diphenylbromomethane and 146 g of triethyl phosphite were stirred under heat at 120 to 130° C. for 8 hours. After reacted, this was cooled and decanted with 500 ml of n-hexane. The solvent was evaporated away, and 284 g of an yellow liquid was obtained. Next, 284 g of the resulting phosphonate and 182 g of p-bromobenzaldehyde were dissolved in 1 liter of dimethylsulfoxide. 113 g of potassium t-butoxide was divided into a few portions, and intermittently added to the solution at room temperature. Next, this was stirred at room temperature for 8 hours, and the reaction mixture was poured into 3.5 liters of water and then extracted three times with 1 liter of chloroform. This was further purified through silica gel column chromatography, and 206 g (yield: 62%) of a white powder was obtained. 20 g of the bromide was dissolved in 50 ml of anhydrous tetrahydrofuran (from Wako Pure Chemicals), and the resulting solution was dropwise added to 65 ml of tetrahydrofuran containing 1.2 g of magnesium, at 50 to 60° C. After the addition, the reaction mixture was refluxed for 1 hour. Thus was prepared a Grignard reagent.

Next, 4.0 g of 1,4-dibromobenzene, 0.6 g of bistriphenylphosphine palladium, 1.8 ml of hydrogenated diisobutylaluminium hydride, and 200 ml of tetrahydrofuran were put into a 300-ml three-neck flask. With keeping the mixture at 50 to 60° C. in an argon atmosphere, the Grignard reagent having been prepared previously was dropwise added thereto over a period of 30 minutes. After the addition, the reaction mixture was stirred for 8 hours. Next, this was left cooled, and then poured into an aqueous 3 N HCl solution. The precipitate thus formed was washed with water, dried, and then purified through silica gel column chromatography, for which the developer was methylene chloride. A white powder was thus obtained, weighing 3.0 g. This is hereinafter referred to as impure DPVTP.

The impure DPVTP was analyzed through high-performance liquid chromatography. The impurities detected were halogen-containing impurities from the starting compounds, such as diphenylvinylbromobenzene, and halogen-containing impurities (intermediates) having been semireacted, such as diphenylvinyl-p-bromobiphenyl. The amount of some these impurities fell between 1000 and 10000 ppm.

Next, the impure DPVTP was purified through sublimation to remove the impurities from it. The boat temperature was 330° C., and the vacuum degree was $10^{-6}$ Torr. As a result, obtained was 2.0 g of a pale yellow milky powder. This is hereinafter referred to as sublimed DPVTP. The sublimed DPVTP was analyzed through high-performance liquid chromatography, which confirmed that the amount of the above-mentioned impurities was all smaller than 1000 ppm.

PRODUCTION EXAMPLE 5

Preparation of Light-emitting Material 9,10-Bis(4-(2,2-diphenylvinyl)phenyl)anthracene (hereinafter referred to as DPVDPAN) is prepared according to the following reaction scheme. This serves as a light-emitting material.

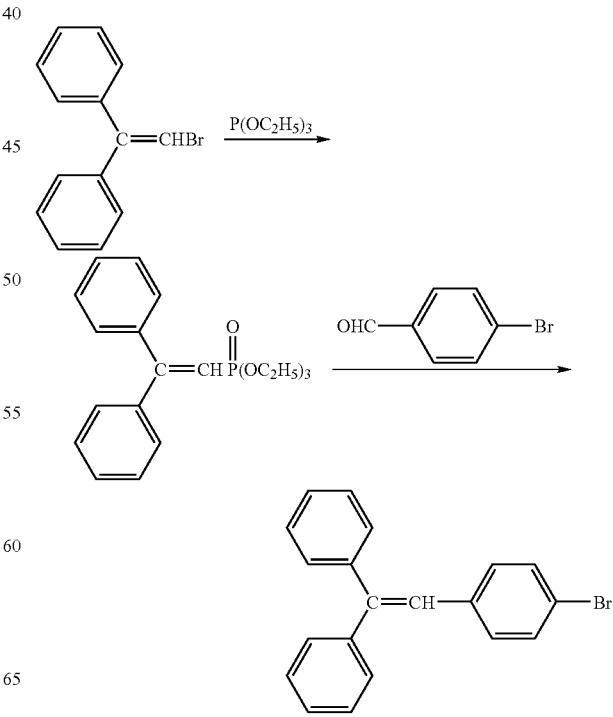

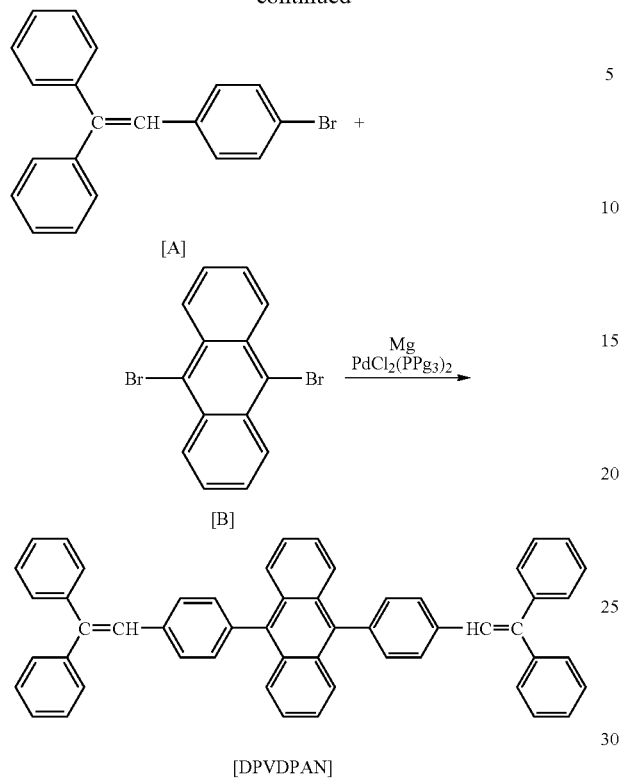

[A]

[B]

[DPVDPAN]

200 g (0.8 mols) of diphenylbromomethane and 146 g (1 mol) of triethyl phosphite were stirred under heat at 120 to 130° C. for 8 hours. After reacted, this was cooled and decanted with 500 ml of n-hexane. The solvent was evaporated away, and 284 g of an yellow liquid was obtained. Next, 284 g of the resulting phosphonate and 182 g (0.9 mols) of p-bromobenzaldehyde were dissolved in 1 liter of dimethylsulfoxide. 113 g of potassium t-butoxide was divided into a few portions, and intermittently added to the solution at room temperature. Next, this was stirred at room temperature for 8 hours, and the reaction mixture was poured into 3.5 liters of water and then extracted three times with 1 liter of chloroform. This was further purified through silica gel column chromatography, and 206 g (yield: 62%) of a white powder was obtained.

Next, ⅕ of a solution of 149.7 g (446.39 mmols, ×3.0 eq) of the compound [A] in 1000 ml of tetrahydrofuran was first added to a dispersion of 16.3 g (669.58 mmols, ×4.5 eq) of magnesium in 500 ml of tetrahydrofuran, in an argon stream atmosphere, and heated at 50 to 60° C. Then, the remaining solution was dropwise added thereto over a period of 1 hour. After the addition, this was reacted at 60 to 65° C. for 5 hours (<1>).

Apart from the reaction <1>, 4.2 g (5.95 mmols, ×0.04 eq) of $PdCl_2(PPh_3)_2$ was added to a solution of 50.5 g (148.80 mmols) of 9,10-dibromoanthracene [B] in 1000 ml of tetrahydrofuran, in an argon stream atmosphere, and then 14.9 ml (14.88 mmols, ×0.1 eq) of isobutylaluminium hydride (in toluene, 1.0 mol/liter) was added thereto. Next, this was reacted at 50 to 55° C. for 4 hours, and the reaction mixture <1> was dropwise added thereto over a period of 20 minutes. After the addition, this was reacted at 65° C. for 18 hours (<2>).

At about 60° C., the reaction mixture was filtered under reduced pressure, and washed with 500 ml of tetrahydrofuran and then twice with 100 ml of acetone in that order. The crystal thus taken out through filtration was dissolved in 14000 ml of dimethylsulfoxide under heat, and recrystallized therein. Thus was obtained a yellowish milky crystal. It weighed 71.0 g, and its yield was 68.7%.

The impure DPVDPAN was analyzed through high-performance liquid chromatography. The impurities detected were halogen-containing intermediates, such as the compound [A] and a semireacted compound of the following formula:

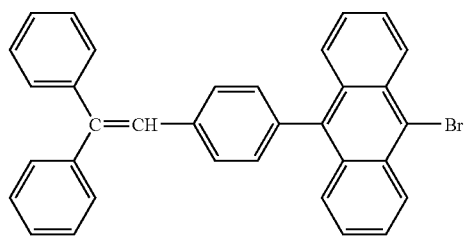

The amount of some these impurities fell between 10000 and 20000 ppm.

Next, the impure DPVDPAN was purified through sublimation to remove the impurities from it. The boat temperature was 380° C., and the vacuum degree was $10^{-6}$ Torr. As a result, obtained was a pale yellow milky powder. This is hereinafter referred to as sublimed DPVDPAN. The sublimed DPVDPAN was analyzed through high-performance liquid chromatography, which confirmed that the amount of the above-mentioned impurities was all smaller than 500 ppm.

EXAMPLE 1

A film electrode of ITO (indium-tin oxide) having a thickness of 100 nm was formed on a glass sheet having a size of 25 mm×75 mm×1.1 mm to prepare a transparent substrate. The substrate was ultrasonically washed with isopropyl alcohol for 5 minutes, then washed with water for 5 minutes, and finally again ultrasonically washed with isopropyl alcohol for 5 minutes. Next, the thus-washed transparent substrate was fixed on a substrate holder in a vacuum evaporation apparatus (by Nippon Vacuum Technology). This vapor deposition apparatus was equipped with a plurality of independent resistance-heating boats of molybdenum, into which were put vaporizing organic compounds. Precisely, 200 mg of the sublimed MTDATA serving as a hole injection material; 200 mg of the sublimed NPD serving as a hole transporting material; 200 mg of the sublimed DPVTP serving as a light-emitting material; 200 mg of DPAVBi serving as a dopant; and 200 mg of the following tris(8-hydroxyquinolinol) (hereinafter referred to as ALQ) serving as an electron transporting material were separately put into those boats.

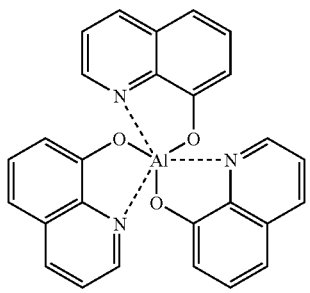

Next, the vacuum chamber of the apparatus was degassed to have a vacuum degree of 1×10⁻⁶ Torr, and the boat with MTDATA being put therein was electrically heated up to 360° C. so that the compound in the boat was vaporized and deposited onto the transparent substrate at a deposition rate of from 0.1 to 0.3 nm/sec to form a hole injection layer of MTDATA having a thickness of 60 nm.

Next, the boat with NPD being put therein was electrically heated up to 260° C. so that the compound in the boat was vaporized and deposited over the hole injection layer of MTDATA at a deposition rate of from 0.1 to 0.3 nm/sec to form thereon a hole transporting layer of NPD having a thickness of 20 nm.

Next, the boat with DPVTP being put therein and the boat with DPAVBi being put therein were electrically heated at the same time to form a mixed emitting layer of DPVTP and DPAVBi having a thickness of 40 nm, in which the ratio of DPVTP/DPAVBi was 40/1 by weight.

Next, the thus-layered substrate was taken out of the vacuum chamber, then provided with a stainless steel mask, and thereafter again fixed on the substrate holder. Next, a cathode-forming, vaporizing material of an aluminium-lithium (Al—Li) alloy having a lithium content of 5 atomic % was vaporized and deposited on the substrate at a deposition rate of from 0.5 to 1.0 nm/sec to form thereon a cathode film having a thickness of 150 nm. During the deposition, the vacuum degree in the chamber was 1×10⁻⁶ Torr.

The thus-fabricated, organic EL device was tested for light emission with 6 V current being applied thereto between the ITO anode and the Al—Li alloy cathode of the device, whereupon the device emitted uniform blue light. The initial data of the device thus driven at 6 V were as follows: The current density was 1.2 mA/cm², the luminance was 100 cd/m², and the emission efficiency was 4.2 lumens/W. With its initial luminance being 100 cd/m², the device was driven at a constant current in a nitrogen atmosphere. In that condition, the half lifetime of the device, within which the luminance thereof was attenuated to 50 cd/m², was longer than 5000 hours.

The constitution and the half lifetime of the organic EL device are given in Table 2.

EXAMPLES 2 to 7

Partly different organic EL devices were fabricated and evaluated in the same manner as in Example 1, for which, however, the organic compounds having been prepared in the above-mentioned Production Examples were combined as in Table 2.

The constitution and the half lifetime of the organic EL devices are given in Table 2.

TABLE 2

| (NPD) Example | Hole Injection Material (MTDATA) | Hole Transporting Material (NPD) | Dopant (DPAVBi) | Light-emitting Material (DPVTP) | Electron Transporting Material (ALQ) | Half Lifetime (hrs) with initial luminance of 100 cd/m² |
|---|---|---|---|---|---|---|
| 1 | sublimed | sublimed | pure | sublimed | pure | 7000 |
| 2 | sublimed | sublimed | pure | impure | pure | 5000 |
| 3 | sublimed | impure | pure | sublimed | pure | 6000 |
| 4 | impure | sublimed | pure | sublimed | pure | 4000 |
| 5 | impure | impure | pure | sublimed | pure | 3500 |
| 6 | impure | sublimed | pure | impure | pure | 3500 |
| 7 | sublimed | impure | pure | impure | pure | 3000 |

INDUSTRIAL APPLICABILITY

The organic EL device of the invention has the advantages of applicability to lightweight, thin and low-voltage driving displays, good luminescent capacity attenuating little even in long-term driving operation, and good durability.

The invention claimed is:

1. An organic electroluminescent device that comprises organic compound layer(s) including at least one organic emitting layer sandwiched between a pair of electrodes, wherein at least one organic compound layer is formed from an organic compound material and said at least one organic compound layer contains lower than 500 ppm of a halogen-containing compound.

2. The organic electroluminescent device as claimed in claim 1, wherein the halogen-containing compound is a halide.

3. The organic electroluminescent device as claimed in claim 1, wherein the organic compound layers are a hole injection layer, an organic emitting layer and an electron injection layer.

4. The organic electroluminescent device as claimed in claim 1, wherein at least one organic compound material to form the organic compound layer(s) is purified through sublimation.

5. The organic electroluminescent device as claimed in claim 1, wherein at least one organic compound material to form the organic compound layer(s) is purified through recrystallization or reprecipitation, or through recrystallization combined with reprecipitation.

* * * * *